United States Patent
Hamilton et al.

(10) Patent No.: US 9,272,139 B2
(45) Date of Patent: Mar. 1, 2016

(54) UNIVERSAL CLOSED-LOOP ELECTRICAL STIMULATION SYSTEM

(76) Inventors: Marilyn J. Hamilton, Carmel, CA (US); John McDonald, III, Baltimore, MD (US)

(*) Notice: Subject to any disclaimer, the term of this patent is extended or adjusted under 35 U.S.C. 154(b) by 112 days.

(21) Appl. No.: 13/807,870

(22) PCT Filed: Jul. 1, 2011

(86) PCT No.: PCT/US2011/042807
§ 371 (c)(1),
(2), (4) Date: Dec. 31, 2012

(87) PCT Pub. No.: WO2012/003451
PCT Pub. Date: Jan. 5, 2012

(65) Prior Publication Data
US 2013/0123568 A1 May 16, 2013

Related U.S. Application Data

(60) Provisional application No. 61/360,690, filed on Jul. 1, 2010.

(51) Int. Cl.
| | | |
|---|---|---|
| *A61N 1/36* | (2006.01) | |
| *A61N 2/02* | (2006.01) | |
| *A61N 1/04* | (2006.01) | |

(52) U.S. Cl.
CPC ........ *A61N 1/36003* (2013.01); *A61N 1/36017* (2013.01); *A61N 2/02* (2013.01); *A61N 1/0484* (2013.01); *A61N 1/36139* (2013.01)

(58) Field of Classification Search
CPC ........... A61N 1/36003; A61N 1/36017; A61N 1/0484; A61N 1/36139
USPC ................................. 607/2, 48, 72
See application file for complete search history.

(56) References Cited

U.S. PATENT DOCUMENTS

| | | |
|---|---|---|
| 4,569,352 A | 2/1986 | Petrofsky et al. |
| 4,642,769 A | 2/1987 | Petrofsky |

(Continued)

FOREIGN PATENT DOCUMENTS

| | | |
|---|---|---|
| EP | 1201266 A1 | 5/2002 |
| EP | 2020250 A1 | 2/2009 |

(Continued)

OTHER PUBLICATIONS

Popovic et al., "Functional Electrical Stimulation Therapy of Voluntary Grasping Versus Only Conventional Rehabilitation for Patients with Subacute Incomplete Tetraplegia: A Randomized Clinical Trial", Neurorehabilitation and Neural Repair, 2010, XX(X) 1-10, Sage, Toronto, Canada.

(Continued)

*Primary Examiner* — Amanda Patton
(74) *Attorney, Agent, or Firm* — George W. Moxon, II; Brian P. Harrod

(57) ABSTRACT

A universal closed-loop functional electrical stimulation system comprising at least one electrode assembly adapted to deliver an electrical stimulation signal to the central nervous system, peripheral nervous system, or muscles of a user, a sensor system adapted to detect a mechanical response to a muscle stimulation signal of at least one muscle associated with a muscle group stimulated through the nervous system or proximate to the electrode assembly. An electrical stimulation device operably coupled to at least one electrode assembly and the sensor system, the electrical stimulation device including a control system to automatically receive feedback from at least one characteristic of the muscle from the detected muscle response and adjust at least one parameter of the muscle stimulation signal in real-time and in response thereto and a programmed microprocessor for controlling said electrical stimulation and receiving input from said sensor system.

20 Claims, 12 Drawing Sheets

(56) References Cited

U.S. PATENT DOCUMENTS

| | | | |
|---|---|---|---|
| 4,724,842 | A | 2/1988 | Charters |
| 4,838,272 | A | 6/1989 | Lieber |
| 4,934,368 | A | 6/1990 | Lynch |
| 5,002,053 | A | 3/1991 | Garcia-Rill et al. |
| 5,014,704 | A | 5/1991 | Alt |
| 5,014,705 | A | 5/1991 | Graupe et al. |
| 5,092,329 | A | 3/1992 | Graupe et al. |
| 5,097,833 | A | 3/1992 | Campos |
| 5,133,354 | A | 7/1992 | Kallok |
| 5,549,656 | A | 8/1996 | Reiss |
| 5,702,323 | A | 12/1997 | Poulton |
| 5,748,845 | A | 5/1998 | Labun et al. |
| 6,029,090 | A | 2/2000 | Herbst |
| 6,065,154 | A | 5/2000 | Hulings et al. |
| 6,145,551 | A | 11/2000 | Jayaraman et al. |
| 6,151,528 | A | 11/2000 | Maida |
| 6,163,725 | A | 12/2000 | Peckham et al. |
| 6,280,461 | B1 | 8/2001 | Glegyak et al. |
| 6,315,009 | B1 | 11/2001 | Jayaraman et al. |
| 6,381,482 | B1 | 4/2002 | Jayaraman et al. |
| 6,445,955 | B1 | 9/2002 | Michelson et al. |
| 6,474,367 | B1 | 11/2002 | Jayaraman et al. |
| 6,652,443 | B1 | 11/2003 | Struppler et al. |
| 6,654,642 | B2 | 11/2003 | North et al. |
| 6,687,523 | B1 | 2/2004 | Jayaramen et al. |
| 6,701,185 | B2 | 3/2004 | Burnett et al. |
| 6,970,731 | B1 | 11/2005 | Jayaraman et al. |
| 6,988,005 | B2 | 1/2006 | McGraw et al. |
| 7,072,721 | B1 | 7/2006 | Trent |
| 7,127,287 | B2 | 10/2006 | Duncan et al. |
| 7,162,305 | B2 | 1/2007 | Tong et al. |
| 7,231,254 | B2 | 6/2007 | DiLorenzo |
| 7,254,444 | B2 | 8/2007 | Moore et al. |
| 7,305,064 | B2 | 12/2007 | Dilmanian et al. |
| 7,346,396 | B2 | 3/2008 | Barriskill et al. |
| 7,499,746 | B2 | 3/2009 | Buhlmann |
| 7,551,957 | B2 | 6/2009 | Whelan et al. |
| 7,565,132 | B2 | 7/2009 | Ben Ayed |
| 7,593,775 | B2 | 9/2009 | Campos et al. |
| 7,603,177 | B2 | 10/2009 | Sieracki et al. |
| 7,610,096 | B2 | 10/2009 | McDonald |
| 7,613,518 | B2 | 11/2009 | Qin et al. |
| 7,636,602 | B2 | 12/2009 | Baru Fassio et al. |
| 7,643,882 | B2 | 1/2010 | Boston |
| 7,725,193 | B1 | 5/2010 | Chu |
| 7,758,490 | B2 | 7/2010 | Pilla et al. |
| 8,112,155 | B2 * | 2/2012 | Einav et al. .............. 607/48 |
| 2003/0158585 | A1 | 8/2003 | Burnett |
| 2004/0044381 | A1 | 3/2004 | Duncan et al. |
| 2006/0155386 | A1 | 7/2006 | Wells et al. |
| 2006/0247095 | A1 | 11/2006 | Rummerfield |
| 2007/0250286 | A1 | 10/2007 | Duncan et al. |
| 2008/0036737 | A1 | 2/2008 | Hernandez-Rebollar |
| 2009/0030482 | A1 | 1/2009 | Barriskill et al. |
| 2009/0030732 | A1 | 1/2009 | Jung et al. |
| 2009/0240305 | A1 | 9/2009 | Lee et al. |
| 2009/0259495 | A1 | 10/2009 | Rosenfeld |
| 2009/0306741 | A1 * | 12/2009 | Hogle et al. .............. 607/54 |
| 2010/0113950 | A1 | 5/2010 | Lin et al. |
| 2010/0114238 | A1 | 5/2010 | Muccio |
| 2010/0114273 | A1 | 5/2010 | Muccio |
| 2011/0004118 | A1 | 1/2011 | Wheeler et al. |
| 2011/0040349 | A1 | 2/2011 | Graupe |

FOREIGN PATENT DOCUMENTS

| | | |
|---|---|---|
| EP | 2020251 A1 | 2/2009 |
| WO | 2005121729 A1 | 12/2005 |
| WO | 2006060934 A1 | 6/2006 |
| WO | 2006113802 A2 | 10/2006 |
| WO | 2008062395 A1 | 5/2008 |
| WO | 2009138961 A1 | 11/2009 |
| WO | 2009141460 A1 | 11/2009 |

OTHER PUBLICATIONS

Thrasher et al., "Rehabilitation of Reaching and Grasping Function in Severe Hemiplegic Patients Using Functional Electrical Stimulation Therapy", The American Society of Neurorehabilitation, 2008, 706-713, 22(6).

Popovic et al., "Neuroprostheses for Grasping", Neurological Research, 2002, 443-52, vol. 24 July, Forefront Publishing Group.

Popovic et al., "Modular transcutaneous functional electrical stimulation system", Medical Engineering & Physics 27, 2005, 81-92, Elsevier.

Popovic et al., "Neuroprostheses for Retraining Reaching and Grasping Functions in Severe Hemiplegic Patients", International Neuromodulation Society, 2005, 58-72, vol. 8, No. 1.

Popovic et al., "Functional electrical therapy: retraining grasping in spinal cord injury", Spinal Cord, 2006, 143-155, vol. 44.

Popovic et al., "Functional electrical stimulation for grasping and walking: indications and limitations", Spinal Cord, 2001, 403-412, vol. 33.

Sinnott et al., "Factors Associated with thoracic spinal cord injury, lesion level and rotator cuff disorders", Spinal Cord 38: 748-753, 2000.

Boninger et al., "Investigating neck pain in wheelchair users", Am. J. Phys. Med. Rehabil. 82: 197-202, 2003.

Baydur et al., "Lung mechanics in individuals with spinal cord injury: effects of injury level and posture", J. Appl. Physiology 90: 405-411, 2001.

Yang et al., "Biomechanical analysis of functional electrical stimulation of the trunk musculature during wheelchair propulsion", Neurorehabil Neural Repair 23 (7), 2009.

Triolo et al., "Implanted electrical stimulation of the trunk for seated postural stability and function after cervical spinal cord injury: a single case study", Arch Phys Med Rehabil 90: 340-347, 2009.

Masani et al., "Postural reactions of the trunk muscles to multi-direction perturbations in sitting", Clin Biomech 24: 176-182, 2009.

Park et al., "The effect of electrical stimulation on the trunk control in young children with spastic diplegic cerebral palsy", J Korean Med Sci 16: 347-350, 2001.

Durmus et al., "Effects of therapeutic ultrasound and electrical stimulation program on pain, trunk muscle strength, disability, walking performance, quality of life, and depression in patients with low back pain: a randomized-controlled trial", Rheumatol Int 2009.

Sadowsy et al., "Activity-based restorative therapies: concepts and applications in spinal cord injury-related neurorehabilitation", Dev Disabil Res Rev 15: 112-116, 2009.

de Groot et al., "Wheelchair propulsion technique and mechanical efficiency after 3 wk of practice", Med Sci Sports Exerc 34: 756-766, 2002.

Mercer et al., "Shoulder joint kinetics and pathology in manual wheelchair users", Clinical Biomechanics 21: 781-789, 2006.

Rice et al., "An analysis of trunk excursion in manual wheelchair users", Proceedings of the RESNA 2004 Annual Conference, Orlando, FL, Jun. 19-22, CD-ROM 2004.

Koontz et al., "Trunk movement patterns and propulsion efficiency in wheelchair users with and without SCI", Proceeds of the ASB 2004 Annual Meeting, Portland, OR, Sep. 9-11, 2004, CD-ROM 2004.

Yang et al., "Surface electromyography activity of trunk muscles during wheelchair propulsion", Clin Biomech (Bristol, Avon) 21: 1032-1041, 2006.

Hiremath et al., "Estimating temporal parameters of wheelchair propulsion based on hand acceleration", Proceedings of the Annual RESNA Conference, Arlington, VA, Jun. 26-30, 2008 CD-ROM.

Ambur et al., "Accelerometry-based classification of wheelchair propulsion patterns using machine learning techniques", Proceedings of the Annual RESNA Conference, Arlington, VA, Jun. 26-30, 2008 CD-ROM.

(56) References Cited

OTHER PUBLICATIONS

Boswell-Ruys et al., "Training unsupported sitting in people with chronic spinal cord injuries: a randomized controlled trial", Spinal Cord 2009.

Lych et al., "Reliability of measurements obtained with a modified functional reach test in subjects with spinal cord injury", Phys Ther 78: 128-133, 1998.

Hincapie et al., "EMG-based control for a C5/C6 spinal cord injury upper extremity neuroprosthesis", Conf Proc IEEE End Med Biol Soc 2007: 2432-2435, 2007.

Graupe et al., "Stochastically-modulated stimulation to slow down muscle fatigue at stimulated sites in paraplegics using functional electrical stimulation for leg extension", Neurol Res 22: 704-704, 2000.

Williamson et al., "Sensor systems for lower limb functional electrical stimulation (FES) control", Med End Phys 22: 313-325, 2000.

Simcox et al., "Performance of orientation sensors for use with a functional electrical stimulation mobility system", J Biomech 38: 1185-1190, 2005.

Kojovic et al., "Sensor-driven four-channel stimulation of paretic leg: functional electrical walking therapy", J Neurosci Methods 181: 100-105, 2009.

Braz et al., "Efficacy and stability performance of traditional versus motion sensor-assisted strategies for FES standing", J Biomech 42: 1332-1338, 2009.

Wong et al., "Smart garment for trunk posture monitoring: A preliminary study", Scoliosis 3: 7, 2008.

Marino et al., "International standards for neurologic classification of spinal cord injury", J Spinal Cord Med 26, Suppl 1, S50-S56, 2003.

Boswell_Ruys et al., "Training unsupported sitting in people with chronic SCI: a randomized controlled trial", Spinal Cord 1-6, 2009.

\* cited by examiner

UNIVERSAL CLOSED-LOOP ELECTRICAL STIMULATION SYSTEM

RELATED APPLICATIONS

The present invention claims the priority of provisional patent application Ser. No. 61/360,690 filed on Jul. 1, 2011, the disclosure of which is incorporated herein by reference.

BACKGROUND OF THE INVENTION

The present invention is to a universal closed-loop, electrical stimulation system which may be integrated with a multi-channel electromyography (EMG) and/or body position sensors (such as, angle accelerometers and gyroscopes) to allow for 1) real-time measurement of body position and movement, 2) autonomous system configuration utilizing closed-loop control and multi-channel capacity, 3) direct operation of neural and muscular structures in the human body and, 4) user-friendly programming capabilities. The electrical stimulation system may produce a variety of electrical outputs such as functional electrical stimulation (FES), transcutaneous electrical nerve stimulation (TENS) and neuromuscular electrical stimulation (NMES). For convenience, the term FES will be used herein to refer to these different electrical stimulation types. The closed-loop FES system of the present invention can also be integrated with wearable garments in its use or combined with electromagnetic devices to deliver further benefits to users.

FES is a method, undergoing continuing development, to restore function to patients with damaged or destroyed neural pathways with microprocessor controlled electrical neuromuscular stimulation and can be used with or without an orthotic device. FES systems use electronics to generate electrical impulses. These impulses are transcutaneous, typically transferred through surface electrodes to stimulate contraction/activity of the muscles that are otherwise dysfunctional or not operating optimally. In order for useful and controlled movements of limbs to be achieved several muscles must usually be operated in concert and sensory feedback closed-loop control is required to alter stimulation patterns in real-time. The impulse delivery is normally coordinated by an algorithm executed under the control of the FES system, the end result being the delivery of a patterned and timed stimulation sequence.

FES systems can be used as an assistive device for neural prostheses to restore functions lost because of neural damage. FES facilitates neuromodulation to help restore motor functions and sensory functions. For example, FES can be used to enhance the function of upper and lower limbs in individuals with paralysis related to spinal cord injury (SCI) or stroke. It has been used to allow standing, walking, cycling, grasping, bowel-and-bladder control, male sexual assistance, and respiratory control in individuals with paralysis related to central nervous system disease (i.e. spinal cord disease (SCD), multiple sclerosis (MS), traumatic brain injury (TBI), spinal cord injury (SCI)). Traditionally, in any nervous system (brain or spinal cord) disease that allows for the (partial) preservation of the nerve pathway to the muscle, FES can be considered to improve either organ anatomy (i.e. muscle mass) or function (i.e. bladder evacuation).

Damage to the mammalian central nervous system ("CNS") can produce devastating physical impairment (paralysis) and associated medical complications and co-morbidities that are life-threatening. Paralysis directly affects most of the organ systems in the body:

a) respiratory system is affected by decrease lung volumes and decreased ability or inability to take a volitional breath.

b) cardiovascular system is affected by the inability to regulate the blood pressure and heart rate.

c) autonomic nervous system is affected and leads to difficulty in regulating body temperature.

d) gastrointestinal and genitourinary systems are affected by the inability to voluntarily control bowel movements and urination. In addition, sexual function is also significantly impaired, to the point of total loss of function.

e) musculo-skeletal system is impaired to volitionally control movement or control abnormal movements. For example, trunk weakness after spinal cord injury leads to trunk instability which further leads to poor posture, difficulty doing activities of daily living (ADL) and a primary contributing factor to the development of upper limb pain and injury.

The use of FES to restore motor function in individuals with neurological impairments is a technique used widely in both clinical practice and paralysis related research institutions. To date however there are very few commercial FES systems that are fully integrated remote systems that adjust stimulation based on sensory feedback in an effort to optimize performance.

As stated, FES has been used to restore certain functions following neural injury or disease. Examples include enhancing the function of the upper limbs in individuals with paralysis related to spinal cord injury (SCI) or stroke, restoring standing, walking and cycling in individuals with paralysis related to central nervous system disease (i.e. spinal cord disease (SCD), multiple sclerosis (MS), traumatic brain injury (TBI), cochlear implants for restoration of hearing, stimulation of muscles and peripheral nerves to restore motor function including hand grasp and release, breathing, and bladder emptying; and deep brain stimulation to treat the motor symptoms of Parkinson's disease (Grill, Warren M., Kirsch, Robert F., "*Neural Prostheses*", *Wiley Encyclopedia of Electrical and Electronics Engineering*, 27 Dec. 1999). Each of these applications work by stimulating neural activity in intact neuromuscular systems to restore control to systems where control has been compromised by injury or disease. FES therapy and neural prostheses devices have also been used with or without locomotor training, such as on a treadmill, or cycle training for individuals with motor paralysis to restore or improve walking. A neural prosthesis device consists of a microprocessor-based electronic stimulator with one or more channels for delivery of individual pulses transcutaneously. The device may also be integrated with a mechanical brace.

An algorithm, that may be stored and controlled by the FES microprocessor, activates channels to stimulate peripheral nerves and trigger muscle contractions to produce functionally useful movements that allow patients to sit, stand, walk, and grasp. Closed-loop FES devices are systems, which provide feedback information on muscle activity and/or joint position, thus allowing constant modification of stimulation parameters, which are required for complex activities such as walking. These are contrasted with open-loop systems where an electronic stimulator only controls the output without considering feedback information.

FES devices have also been developed for patients with foot drop. Foot drop is weakness of the foot and ankle that causes reduced dorsiflexion and difficulty with ambulation. It is often a result of damage to the central nervous system such as stroke, incomplete spinal cord injury, traumatic brain injury, cerebral palsy and multiple sclerosis. Stimulation of the peroneal nerve has been used as an aid in raising the toes during the swing phase of ambulation. Examples of such devices used for treatment of foot drop are the Innovative Neurotronics (formerly NeuroMotion, Inc.) WalkAide®, Bioness radio-frequency controlled NESS L300™, and the Odstock Foot Drop Stimulator.

FES can assist standing and primitive walking in SCI individuals has been achieved utilizing the Parastep® Ambulation System. Using this system, only spinal cord injury patients with lesions from T4 to T12 were considered candidates for ambulation as the energy requirements for the individuals with higher injuries were considered prohibitive and individuals with lower neurologic injuries would not respond to the electrical stimulation parameters utilized by the Parastep. Using percutaneous stimulation, the device delivers trains of electrical pulses to trigger action potentials at selected nerves at the quadriceps (for knee extension), the common peroneal nerve (for hip flexion), and the paraspinals and gluteals (for trunk stability). Patients use a walker or elbow-support crutches for further support. The electrical impulses are controlled by a computer microchip attached to the patient's belt that synchronizes and distributes the signals. In addition, there is a finger-controlled switch that permits patient activation of the stepping. Other devices added a reciprocating gait orthosis (RGO) to an FES system but the orthosis used was a cumbersome hip-knee-ankle-foot device linked together with a cable at the hip joint and the use of this device was limited by the difficulties in putting the device on and taking it off (Hirokawa, Gimm, Le, Solomonow, Baratta, Shoji, D'Ambrosia, "Energy Consumption in Paraplegic Ambulation Using the Recipriocating Gait Orthosis and electrical stimulation of thigh muscles", Arch Phys Med Rehabilitation 1990 August; 71(9):687-94). Neuromuscular stimulation is also proposed for motor restoration in hemiplegia and treatment of secondary dysfunction (e.g., muscle atrophy and alterations in cardiovascular function and bone density) associated with damage to central motor nerve pathways.

Despite the described devices, a great need therefore remains for universal, closed-loop, portable, easy to use interchangeable and multi-functional systems that partially or completely restore lost or impaired motor and sensory function in individuals suffering from disruptions of motor and sensory function due to damage of the CNS. The commercial market translation of surface FES systems has been limited in capability and scope. Surface FES systems for general clinical use are limited to 2-4 channel open-loop systems or simple biofeedback closed-loop systems (e.g. NeuroMove™ NM900 and Thought Technology MyoTrac Infiniti). FES cycling uses knowledge from the machine itself (e.g. crank angle and/or cadence) to adjust the timing of muscle activation. A few commercial products have coupled movement sensors such as accelerometers and gyroscopes in a closed-loop fashion with surface FES, but they have limitations, such as for example, Innovative Neurotronics WalkAide which has 1 FES channel and 1 accelerometer. Bioness NESS L300 has 1 FES channel and 1 foot switch. There are a few commercial products that provide multi-channel movement sensors but not in combination with FES (Delsys Trigno Wireless). There are few patents and no closed-loop products that currently target trunk function in SCI. What is needed to improve clinical care and evidence-based user outcomes is a smart multi-channel, 3D position sensor and/or EMG regulated, closed-loop FES system that can automate stimulation (i.e. smart system) to maximize physical reconditioning and spontaneous neurological recovery with the capacity to be used in a clinical center, gym or home-based environment while being monitored at a distance.

Discovery of new control approaches, which can exploit voluntary movements to drive the body in an intended way, has been of great interest to scientists and clinicians. Electromyographic signals have been investigated to a large extent as a means to predict the level of muscle activation for performing activity or adjusting stimulation upon sensing fatigue. Moreover 3-D movement sensors to automate stimulation signals have been used in several studies (Williamson R and Andrews B J, "Sensor systems for lower limb functional electrical stimulation (FES) control", Med Eng Phys 22: 313-325, 2000; Simcox S, Parker S, Davis G M, Smith R W and Middleton J W, "Performance of orientation sensors for use with a functional electrical stimulation mobility system", J Biomech 38: 1185-1190, 2005). Patented invention approaches include (U.S. Pat. No. 7,346,396 Barriskill et al., U.S. Pat. No. 7,162,305 Tong et al.). Despite the substantial evidence that automating stimulation is more effective than using manual methods in a variety of rehab applications, real-time closed-loop FES control of patient parameters is not widely available to clinicians.

Therefore, a need exists for a universal closed-loop FES system that would measure, monitor, stimulate and provide sensory feedback closed-loop real-time control for the human nervous system. This can be used in sports and fitness for motion capture and analysis; toning, tightening and strengthening muscles; and cardiovascular exercise. It can also be used for people with paralysis strengthening muscles, nerves and restoring motor and sensory function. Scientifically this system can be used to validate outcome measures in SCI related to research. Currently, trunk function assessment in SCI individuals is significantly limited by the inability to perform a detailed clinical examination. There is no current tool to objectively assess the trunk muscle activity. Without a valid and practical means to measure the neurologic function between T2-T12, assessing the safety and efficacy of potential therapeutic interventions in humans will seriously be hampered. Creating a critical outcome assessment tool for thoracic spinal cord function will have the largest impact on future human clinical trials, rehabilitation strategies, and understanding the physiologic basis (neuroplasticity) for activity-based restorative therapies (ABRT).

SUMMARY OF THE INVENTION

The present invention embodies a novel universal, multi-channel, closed-loop functional electrical stimulation system (closed-loop FES system) that may be integrated with a multi-channel electromyograph (EMG) and body position sensors (such as, angle accelerometers and gyroscopes) and are controlled by a wearable computer system with the bandwidth to process a large amount of data in real-time integrating information through multi-array electrodes systems. The multiple-array electrodes include stimulation and sensory electrodes. The system allows real-time measures, autonomous configuration, closed loop control and multi-channel input/output capacity and end-user programming capabilities. The system provides multiple output stimulation types such as FES, TENS, NMES and other through the customized software architecture. The system can be further integrated with other devices such as wearable garments or electromagnetic devices to deliver other benefits to users.

In one embodiment of the present invention an automated adaptive functional electrical closed-loop stimulation system is described, including, at least one electrode assembly adapted to deliver an electrical stimulation signal to the central nervous system, peripheral nervous system, or muscles of a user. The system also includes a sensor system adapted to detect a mechanical response to a muscle stimulation signal of at least one muscle associated with a muscle group stimulated through the nervous system or proximate to the electrode assembly. The system further includes an electrical stimulation device operably coupled to at least one electrode assembly and the sensor system, the electrical stimulation device including a control system operable to automatically receive feedback from at least one characteristic of the muscle from the detected muscle response and adjust at least one parameter of the muscle stimulation signal in real-time and in response thereto to deliver an adjusted muscle stimulation signal. The system also includes a programmed microprocessor for controlling said electrical stimulation and receiving input from said sensor system, including means for comparing said electrical stimulation and said mechanical response based upon the input from the sensor system and the means for comparing, where the electrical stimulation and the detected muscle response comprises a plurality of reaction pulses.

The present invention stimulates muscle groups selectively, not only to restore motor function to persons with disabilities and/or paralysis, but also address FES exercise for people who are overweight (and those that want to "improve their game") and those looking for ways to optimize the aging process and reverse or prevent loss of cells, neural connections and functional efficiency. The present invention will improve physical conditioning and fitness that will reduce hyperlipidemia, reduce cardiovascular risk factors, reduce stroke risk factors, reduce sensitivity for depression, optimize cognitive performance and improve physical conditioning. The present invention will also improve the longevity of performance in general sports, and/or advanced sports performance by optimizing, extending and tracking training. With the FES closed-loop system, elite athletes can identify areas of need, develop applications for novel training techniques and push themselves to optimize neuromuscular function. Athletes will be able to overcome their body's natural brakes.

Current FES systems have limited and isolated clinical applications and are largely restricted to center based-treatment and therefore accessible to only a small percentage of patients and restricted temporally in time to the acute and sub acute clinical care setting. Because of the universality and portability of the present invention, it may be used in many fields such as in a rehabilitation setting, outpatient setting, home or in athletic facilities. The present invention can be used for acute and chronic medical issues as well as everyday use for sports performance and fitness. Additionally, the system's customization features allows researchers to develop different tools used as inputs and outputs for different projects.

BRIEF DESCRIPTION OF THE DRAWINGS

The present invention will now be described by the way of a non-limiting example, with reference to the attached drawings in which.

DETAILED DESCRIPTION OF THE INVENTION

Figure 1:
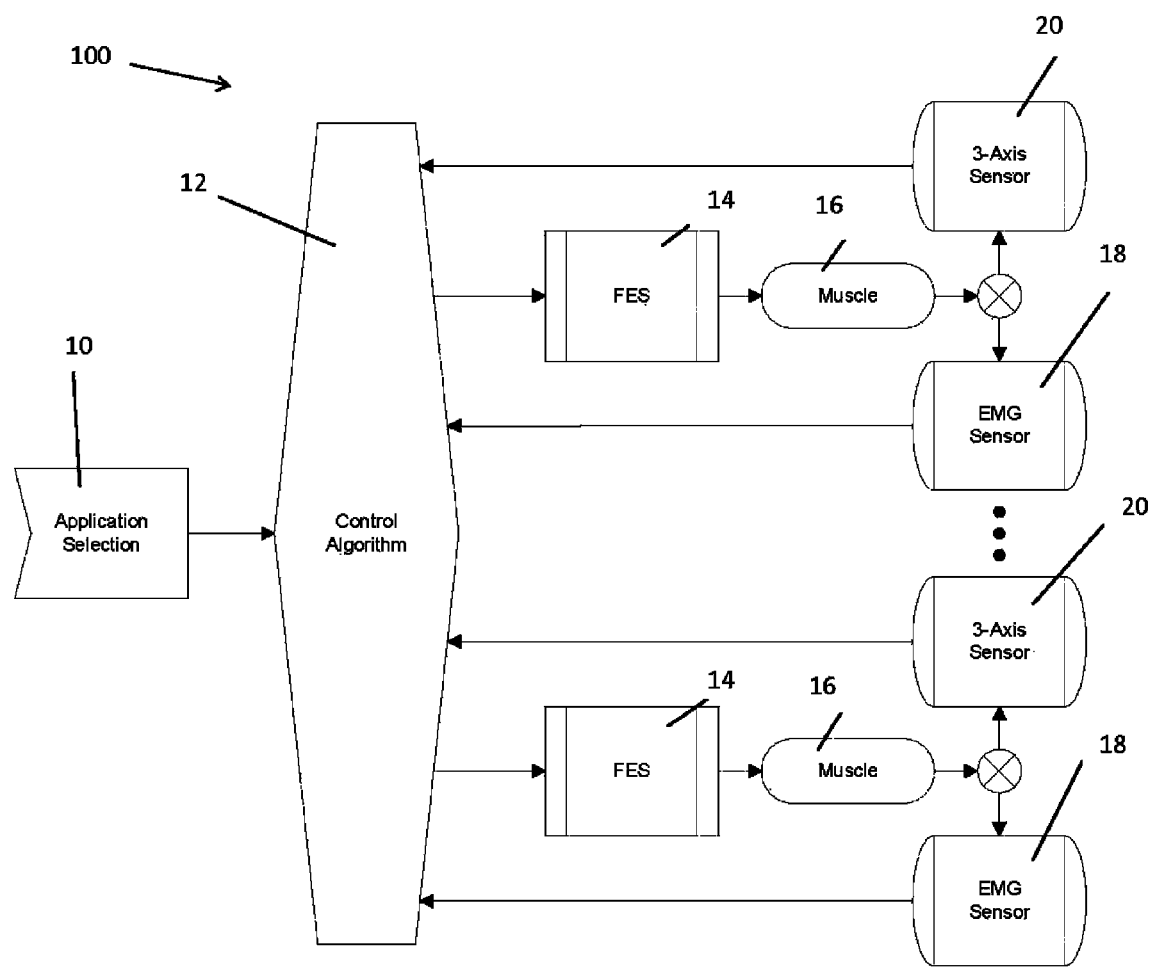
FIG. 1 is block diagram showing the FES system of the present invention.

The present invention embodies a novel universal closed-loop, multi-channel electrical stimulation system, that can be integrated with multi-channel electromyography (EMG) and body position sensors (such as, angle accelerometers and gyroscopes) and are controlled by a wearable computer system with the bandwidth to process a large amount of data in real-time integrating information through multi-array electrodes systems. The multiple-array electrodes include stimulation and sensory electrodes. The system allows real-time measures, autonomous configuration, closed loop control and multi-channel input/output capacity and end-user programming capabilities. The FES system of the present invention may allow for control of the trunk, upper and lower extremity, pelvic and low back muscles and other parts, or combination of parts, allowing performance of cardiovascular exercise, measurement of predictive movement, muscle enhancement, intermittent stimulation for healing of skin ulcers and deep tissue stimulation.

The FES system of the present invention will serve as either a passive measurement device, a data-monitoring device or, as a measurement and monitoring device combined with dynamic stimulator all-in-one application integrated with intelligent garments. The system may also be a Continua Health Alliance compliant remote monitoring device. The FES system of the present invention will deliver electrical stimulation to the central nervous system, the peripheral nervous system and directly to the muscles of the user in order to achieve a multitude of end results, including, but not limited to 1) motion capture and movement analysis, 2) cardiovascular exercise, 3) measurement of predictive movement, 3) toning, tightening and strengthening muscles, 4) cardiovascular exercise, 5) providing specific organ functions, including upper and lower limbs and extremity movement and trunk movement and stability, 6) muscle hypertrophy, 7) restoration of lost motor movement and enhancement of current motor function and abilities, 8) control of muscle spasticity, 9) deep tissue stimulation, and 10) healing of skin ulcers. The FES system of the present invention can be further integrated with other devices such as, for example, wearable garments or electromagnetic devices to deliver further benefits to users.

The present invention can be used to quantify motor and sensory function in neurologic diseases. For example, it can measure motor function of the thoracic spinal cord using a smart sensor device, such as electromyography and motion sensors, and provide a lightweight closed-loop FES system for stimulating the core muscles' functional performance. The present invention enables real-time closed loop control on a modular hardware platform designed to accommodate a large array of feedback sensors and stimulation channels, enabling capabilities previously inaccessible to clinical practice. Further, the present invention will provide a new quantifiable assessment tool for thoracic motor function using a trunk garment with imbedded electrophysiological sensors, which will record axial muscle recruitment and trunk extension, flexion, lateral flexion, and rotation in individuals with paralysis during unsupported sitting via surface EMGs and measure trunk excursion during specific activity-based tasks (i.e. seated forward reach and lateral lean) using body position sensors.

The present invention consists of a state-of-the-art embedded system with modular architecture and peripheral sensory devices. For example, the present invention utilizes sensory data on reach and propulsion activities in conjunction with control algorithms from the data collected to provide operation within the requirements for real-world activities. Surface EMG and movement sensor data can be synthesized to determine trunk muscle activity (amplitudes and timing) and sensor thresholds for classifying wheelchair propulsion activity (e.g. ramp ascent versus level propulsion) and cycle phasing. The system receives and drives input/output signals in accordance with design specifications.

The present invention incorporates 3-axis accelerometers on the body to characterize upper extremity activity and to understand the impact of wheelchair use on the development of repetitive strain injuries. We have found that local peaks in axis and resultant hand acceleration closely match the start instances of recovery (hands off rim) and propulsion (hands on rim) phases detected by the SMART Wheel, which is considered a standard instrument and is used as the reference method. The system of the present invention enables the ability to objectively quantify motor function of the trunk. The present invention employs a system (e.g. surface EMG and 3D sensor data) to match the input with the functional requirements.

The present invention is directed to an automated adaptive FES system comprising at least one electrode assembly adapted to deliver an electrical stimulation signal to the central nervous system, peripheral nervous system, or muscles of a user, a sensor system adapted to detect a mechanical response to a muscle stimulation signal of at least one muscle associated with a muscle group stimulated through the nervous system or proximate to the electrode assembly, and an electrical stimulation device operably coupled to at least one electrode assembly and the sensor system, the electrical stimulation device including a control system operable to automatically receive feedback from at least one characteristic of the muscle from the detected muscle response and adjust at least one parameter of the muscle stimulation signal in real-time and in response thereto to deliver an adjusted muscle stimulation signal; and a programmed microprocessor for controlling said electrical stimulation and receiving input from said sensor system, including means for comparing said electrical stimulation and said mechanical response based upon the input from the sensor system or a data base of preferred responses and the means for comparing, wherein the electrical stimulation and the detected muscle response comprises a plurality of reaction pulses.

The present invention, as seen in FIG. 1, is a modular system 100 that provides closed-loop surface FES functionality. In use, a particular application will be chosen and instructions will be input into an application selection 10. This can be a touch screen display or other appropriate device. The input from application selection 10 will go to a digital computer system having a computer readable memory and processor which is controlled by a control algorithm 12. The algorithm will in turn determine the appropriate signal pattern for the functional electrical stimulator (or FES) 14 to apply to the appropriate location in the nervous system and hence to the appropriate muscle(s) 16. The signal can be transmitted via an electrode placed at the appropriate location(s) for treatment or stimulation. When the muscle responds, an electrical signal is generated by the muscle and the electrode(s), which could be the same or different than those used for the FES, will pass the electrical signal to an electromyograhic sensor 18 which will detect the signal and feed it back to the processor 12. At the same time, a motion sensor 20, such as a 3-axis sensor, will provide another feedback signal for the processor 12. By comparing the required or desired stimulation pattern, as inputted from the application section 10, the electrical signal to be outputted via the FES 14 can be adjusted. The system can also employ an electrical filter means for eliminating unwanted signals and noise from the input signals. Additionally, a means for amplifying the input signals and controlling the amplification range of the input signals may be employed.

The present invention will provide versatility via the programming so that it can, for example, be used to stimulate the trunk muscles of a user and then used to stimulate the leg muscles of another user, although not at the same time. Or, it could be used by the same user, but for different muscle groups. Thus, the present invention is versatile and adapting it for different uses is simple. The stimulation of the trunk muscles would be done, for example, to facilitate a person sitting up, improving posture, improving respiration, or moving from one position to another, where there is no longer such functionality in that person, but where the nervous system can be accessed and stimulated. That need would be different from the need to move a leg, but the programming of the processor via the appropriated algorithm would mean that the device and system would not need to be reconfigured to function and the adjustment could be done via the software for the device.

Further, the capability of the system means that multiple electrodes, or a garment which contains and/or supports electrodes, could be used since the processor can be programmed to go through a selection process to determine the appropriate electrodes for the appropriate procedure. Such procedures are known, such as for example, the one set forth in an article by S. B. O'Dwyer et al., "An electrode configuration technique uses an electrode matrix arrangement for FES-based upper arm rehabilitation systems", *Medical Engineering & Physics* 28 (2006), pages 166-176, which is incorporated herein by reference. Additionally, microelectrode array does not need to be limited to garments but may include technologically advanced skin interface microelectrode systems.

Figure 2:
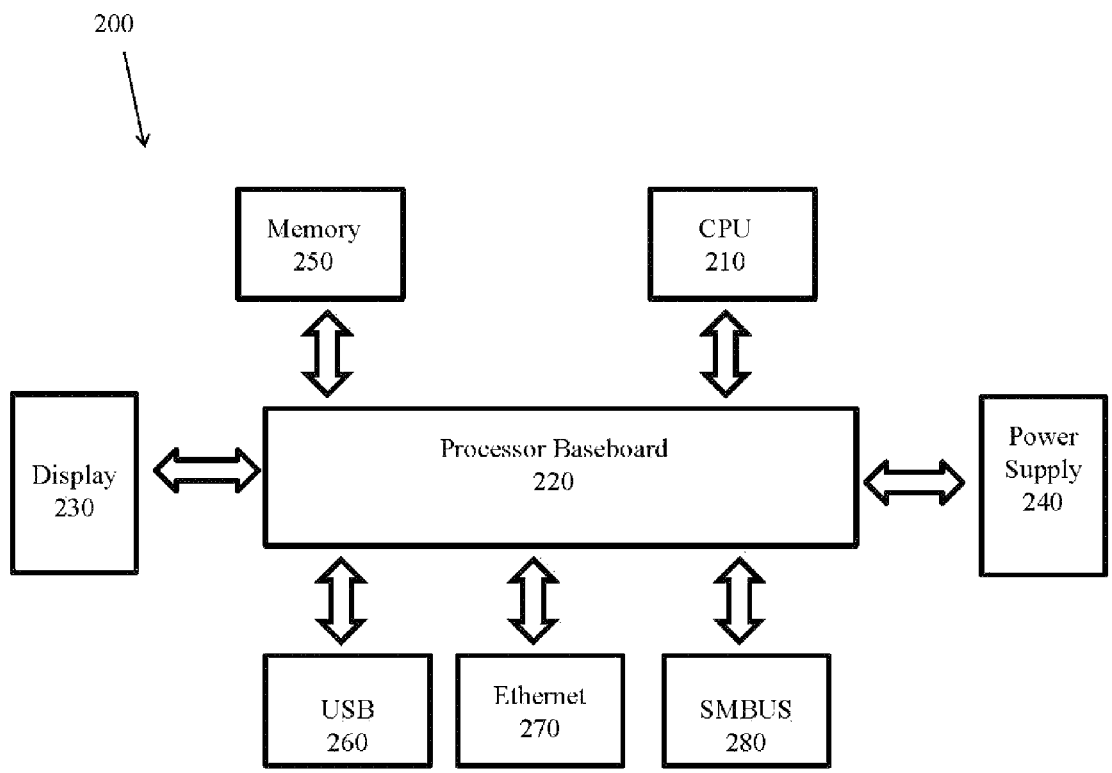
FIG. 2 is a block diagram of the present invention showing the remote module.

As seen in FIG. 2, the system 200 can be a computer, for example a remote module (RM). The RM will support the surface FES peripheral, which provides transcutaneous neuromuscular stimulation. The RM may be based on a processor such as an Intel® Atom Processor, although other appropriate processors could be employed provided they have the high speeds required, and the same versatility, flexibility, and transportability, and which incorporates high speed I/O ports. In one example, the RM may incorporate up to 32 I/O ports centered on an Altera Stratix-II™ GX field programmable gate array for control. The RM could also employ 6 USB ports and have wireless capability. Further, the RM could be a "flexible computer", which would be one that provides the same processing, but is incorporated in a fabric or is part of a fabric or technically advanced skin interface microelectrode system so that the person being treated could wear the processor without the need for bulk or weight.

There is no limit to the number of ports, and the ports can be employed to support a star topology, tree topology, or any similar topology, which extends the reach of the sensors/stimulators, thus enabling the attachment for hundreds of sensors for feedback and control. As noted, the system can function as a remote module, e.g., it could be wireless and not be connected via a wire, or it could function as a wired system, depending on the needs involved. The RM will support two types of "peripheral components", for example, a surface Functional Electrical Stimulation—Electromyography (FES-EMG) peripheral which provides transcutaneous neuromuscular stimulation as well as surface electromyography and a peripheral with a combined 3-Axis accelerometer and 3-Axis gyroscope (3-D sensor) which provides time-space limb kinematics feedback in real-time. A modular use of the peripherals allows clinicians or coaches to "mix and match" and "plug and play" any number in any combination to satisfy their needs.

The present invention will be explained in terms of a 5 port system, but this is only exemplary, and more ports could be employed or fewer ports could be combined with a star topology approach. The present invention is not limited to 5 ports and could comprise more or less ports or could encompass a star, tree, or other topology. Further, the modular approach allows for the combination of several units to obtain the necessary multiplicity. In a preferred embodiment, the present invention may employ more than 10 electrodes. The electrodes may be embedded in the wearable garment associated with the present invention. It is possible to employ more than 100 electrodes. By employing a large number of electrodes, the system is able to stimulate multiple muscles. Preferably, 8 to 10 muscles may be stimulated. Still further, electrodes can be placed in numerous spots, or be available via the use of clothing, covers, wraps and/or advanced skin interfaces to address nerves and muscles and then the system can evaluate which electrodes need to be active for the desired treatment and which electrodes are near vital organs and need to be deactivated.

FIG. 2 shows an embodiment of the current invention. The system 200 of the present invention is comprised of a CPU 210 and a baseboard 220 that hosts a touch sensitive display 230 for user interaction; input and output ports, such as USB 260, Ethernet 270, System Management Bus (SMBUS) 280, and a power supply 240. The display 230 may be an 800×480 4.8" TTL TFT display with four-wire touch sensitive overlay. In one embodiment, the CPU 210 operates at a speed of at least 1.0 gigahertz and adjusts FES parameters within 10 milliseconds.

As can be appreciated, these components exemplify the present invention and so should not be considered limiting. These devices are bundled together into a single mini-chassis that satisfies passive cooling needs. Five high speed serial ports 260 such as 5 USB 2.0 Micro-AB ports support sensor/FES daisy-chain capability. The Ethernet port 270, such as a GigB Ethernet RJ-45, will provide for secure remote communications. The SMBUS/USB 280 Type A will provide lightweight communication, typically to the power supply 240. The power supply 240 may be a 1.4-12 VDC power supply connected to a Li-Ion battery pack 2S1P, 7.4V 1200 mAH.

The FES functionalities of the RM 200 have been chosen to facilitate US Food and Drug Administration clearance, and thus has similarities like other FDA cleared surface powered stimulators (e.g., Simcox et al. 2004). The FES functionalities include amplitude of 0-140 mA, a pulse width: 0-500 us, a frequency of 0-500 Hz, a pulse waveform that is biphasic, charged balanced. The EMG functionalities could include, for example and depending upon the treatment, a bandwidth of 0.05 Hz to 150 Hz, 60 Hz/50 Hz suppression, and electrocardiogram (ECG) artifact detection/blanking, as may be required to detect and mark the signals.

The EMG sensors incorporate electrode conductivity reading. The EMG circuitry shares the same electrode pads as the FES circuitry to minimize electrode placement and maximize EMG muscle feedback quality. The 3-D sensor incorporates both 3-Axix gyro and 3-Axis accelerometer capability into a combined sensor, which is necessary for proper sensing and feedback to the control unit. The 3-D sensor functionalities include sagittal, coronal, and transverse angle, angular velocities in 3-D and accelerations in 3-D. The rotational and accelerometer readings are measurable in one degree increments on all three axes and read via the USB 2.0 port. The 3-D Sensor peripheral USB 2.0 port is based upon industry standards.

One of the full-speed/low-speed USB ports 260 is dedicated to internal needs, the Touch Sensitive Interface device, display 230. The Touch Sensitive Interface device, display 230, requires a USB 1.0 low-speed port for operation. To satisfy this internal need, one of the six ports capable of full-speed and low-speed signaling is internally committed, leaving only five ports for external utilization.

The system 200 may comprise three Universal Host Controller Interfaces (UHCI) and one Enhanced Host Controller Interface (EHCI). Each UHCI supports two (2) USB 1.1 ports. The EHCI supports two (2) high-speed USB ports (for internal utilization only) and can multiplex over the six UHCI ports. Preferably, the EHCI may support up to fifteen (15) FES/EMG peripherals and sixteen (16) 3-Axis peripheral sensors on a single USB internal Hub port, however the EHCI may support more or less. Additional peripheral components can be accommodated by clustering multiple Remote Modules via GigE Ethernet ports. Up to a dozen RMs can be clustered together.

The RM 200 operates on a Real Time Operating System (RTOS), and a LCD touch screen with a basic user interface for selecting and tweaking stimulation strategies and sensor channels and parameters. The closed-loop control algorithms are implemented in the RTOS. The software test routine operating on the remote module will adjust and drive every possible parameter and the specification outcome will be validated. The software test routine on the RM will combine every parameter in every combination and validate that the remote module operates as specified. Validation of a control loop latency of 10 ms or better will be employed using the existing internal processor performance clocking mechanisms and the default utilities provided by Wind River.

The RM 200 utilizes standard protocols for physical signal input and output. Two key aspects of the RM 200 cover all input and output capability. The first key aspect consists of five USB 2.0 ports to drive peripheral components. The second key aspect is the Graphical User Interface (GUI) including all programmable device parameters that drive all signal input and outputs.

The USB 2.0 peripheral component ports are capable of driving any combination of peripheral components. The EMG circuit will use an industry standard EMG wave-form generator (such as is available from Fluke). Input EMG test wave-forms will be read and validated via the USB 2.0 port. These parameters will be driven via the USB 2.0 port. A variable resistor in the test system will be adjusted from zero ohms to 10 mega-ohms in 500 ohm increments for each parameter and, when needed, the output signal can be validated via an oscilloscope reading.

Because the combination of FES and EMG functions share electrodes, key signal protection circuitry is designed into the EMG input signal path to ensure that high-voltage FES signals do not interfere with EMG sampling Inherent and dynamic changes in electrode to surface skin conductivity are a well-known issue in surface FES. To combat this problem, the FES circuit in the present invention is designed as a current controlled drive. In addition to this, junction conductivity reading circuitry has been designed into the EMG circuit that allows dynamic conductivity readings to be taken in real-time.

FIGS. 3-8 show examples of an algorithm for use in the present invention. The present invention utilizes an algorithm which reflects outcome measure for functional capacity within various neurologic levels, such as for example, thoracic SCI, and assesses postural control in the seated position in response to perturbations using motion analysis and gyroscope technology. The algorithm facilities providing a trunk core strengthening FES based upon both sensor technologies and closed loop FES controlled stimulation.

Electrical stimulation signals are applied to the selected muscles at a predetermined frequency, pulse width, and amplitude, and work output by the muscles in response to stimulation signals determined over a fixed period of time. The work output is compared to a defined value which can be a target value or a value measured during a previous stimulation period. The amount of electrical energy coupled into the muscles by the stimulation signals is varied in response to the results of the comparison in order to maximize the amount of work output by the muscles during a treatment period. This is accomplished by adjusting the frequency and/or pulse width during stimulation treatment in response to the work output measured. For example, if it was desired to move a leg, the programmed microprocessor could produce hip movement by generating control signals for stimulation transducers which stimulate the iliacus, hamstring, and gluteal muscles. The microprocessor produces knee movement through generation of control signals for stimulation transducers which stimulate the quadriceps and hamstring muscles. Finally, the microprocessor produces ankle movement through generation of control signals for stimulation circuits which stimulate the gastrocnemius and tibialis muscle groups. As the hip, knee and ankle motion progresses, corresponding feedback signals are generated by sensors mounted on the body, and these feedback signals are applied to the microprocessor for closed-loop control of the stimulation control signals. Movement restriction means are provided for limiting movement of the hips and knees to a common plane, thereby limiting the number of muscle groups requiring stimulation. In addition, motion sensors would provide an additional feedback signal and allow for further adjustment.

Since an electrical stimulation signal will be affected differently in different people, the feedback is helpful in evaluating whether or not the proper signal was delivered to the proper area. Some of the variance, given as examples and not considered limiting, can be due to a person's tissue properties, physical activity levels, amounts of body fat, tissue layer thickness, depth of nerve in the muscle, and how the electrode is making contact with the skin.

The present invention provides the capability to apply any type of electro-medical treatment. For example, one exemplary embodiment of the multi-functional electro-medical device in accordance with the present invention is programmed to apply interferential current stimulation, high voltage muscle stimulation as well as pulsed muscle stimulation treatments. With the ability to provide interferential current stimulation, the multi-functional portable electro-medical device of the present invention provides the ability to be used universally for a variety of treatments. Although the term FES is used herein, the multi-functional portable electro-medical device in accordance with the present invention may be programmed to apply many other types of electro-medical treatment such as NEMS, TENS, micro current, high voltage, constant voltage or pulse width, and the like.

To create real-world "natural" movement via FES, two key capabilities are needed. Most "natural" movement involves a multitude of muscles (more than 4-6) working together in various degrees of contribution and coordinated timing. The present invention is able to drive large numbers of muscles, in varying degrees, and in a coordinated manner. This can be contrasted with crude FES technology which can force muscle movement, but that movement is strongly distorted (i.e. either dysfunctional or "robot like"). Any re-connection through the damaged spinal cord due to neural restoration achieved through therapeutic measures like ABRT will ultimately be limited, therefore only allowing for "robot like" functionality. Sensing of muscle movement, as well as other key factors like fatigue, combined with capabilities for constant FES adjustment based upon that sensing enable real-world "natural" movement. This is facilitated via real-time feedback and closed-loop control. The present invention is a device that is wearable, can drive a large number of muscles, provide sensing for those muscles, and manage real-time closed-loop control via computer processing capability. Further, by emulating real-world "natural" movement, it might be possible to accelerate the re-mylenation and re-growth process.

Figure 3:
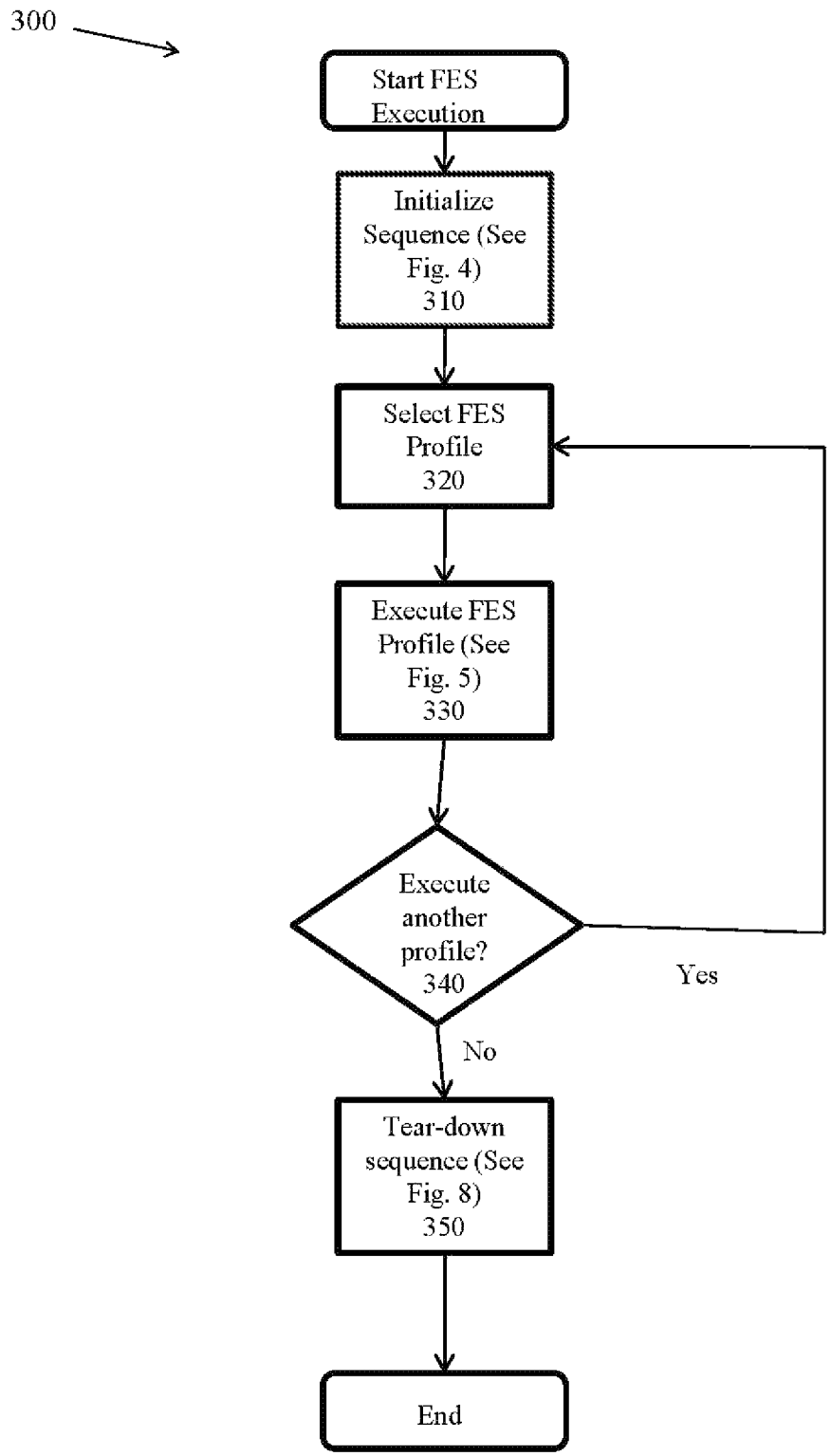
FIGS. 3-8 are flow diagrams showing an example of an algorithm employed with the present invention.
Figure 4:
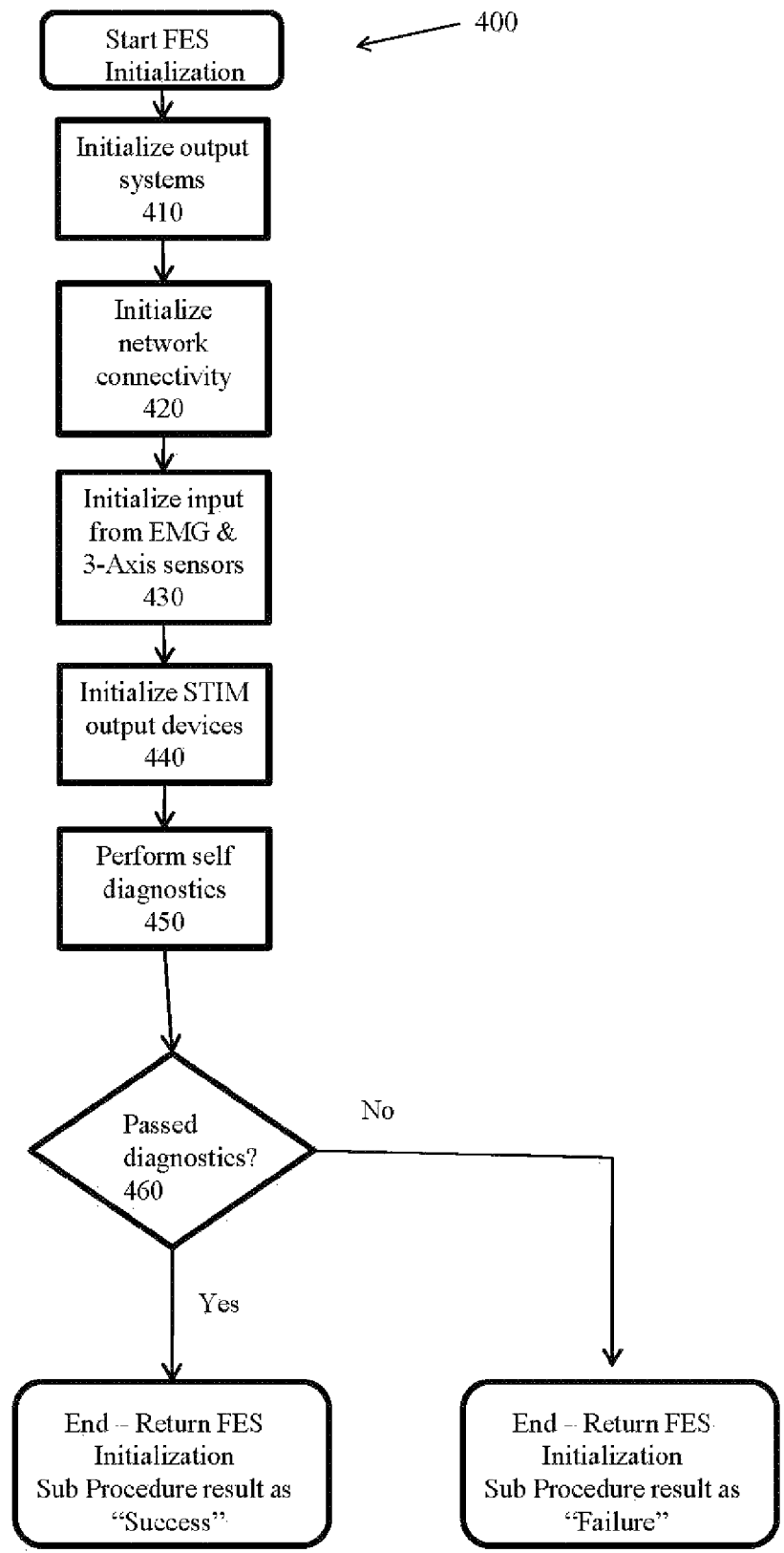

A more detailed version of the process and algorithm shown in FIGS. 3-12 will now be described. FIGS. 9-12 show a general selection process that utilizes the algorithm shown in FIGS. 3-8. In FIG. 9, the end-user may begin the application and at step 910, the hardware initiation sequence, shown in FIGS. 3 and 4, are executed. Procedure 300, shown in FIG. 3, includes the steps of initializing the system 310, selecting a FES profile 320, executing the FES profile 330, determining whether to execute another FES profile 340 and a tear down sequence 350.

FIG. 4 shows the FES initialization sub-procedure 400. Sub-procedure 400 includes the steps of initializing output systems 410 and initializing network connectivity 420, such as wireless or hardwired network. Sub-procedure 400 also includes the steps of initializing input from EMG & 3-Axis sensors 430 and initializing STIM output devices 440. The sub-procedure 400 may also include performing self-diagnostics at step 450 to ensure that the system and devices are working properly. If the self-diagnostic test is successful, the sub-procedure 400 returns a result of "Success" and procedure 300 continues. However, if the self-diagnostic test is unsuccessful, the sub-procedure 400 returns a result of "Failure" and the sub-procedure may abort.

Referring back to FIG. 9, after initialization, an end-user has the option to select a saved program at 920. A display of the saved programs for selection may be displayed at 930. The sequence to save a program is described in more detail in FIG. 11. If the end-user would like to begin a new program, the end-user selects a stimulation program at 940. For example, selected program may provide stimulation to the legs, trunk, legs or hands. At 950, the stimulation points for the selected program are listed and selected. For example, in an arm stimulation program one or more points on one or more muscles may be defined.

Figure 10:
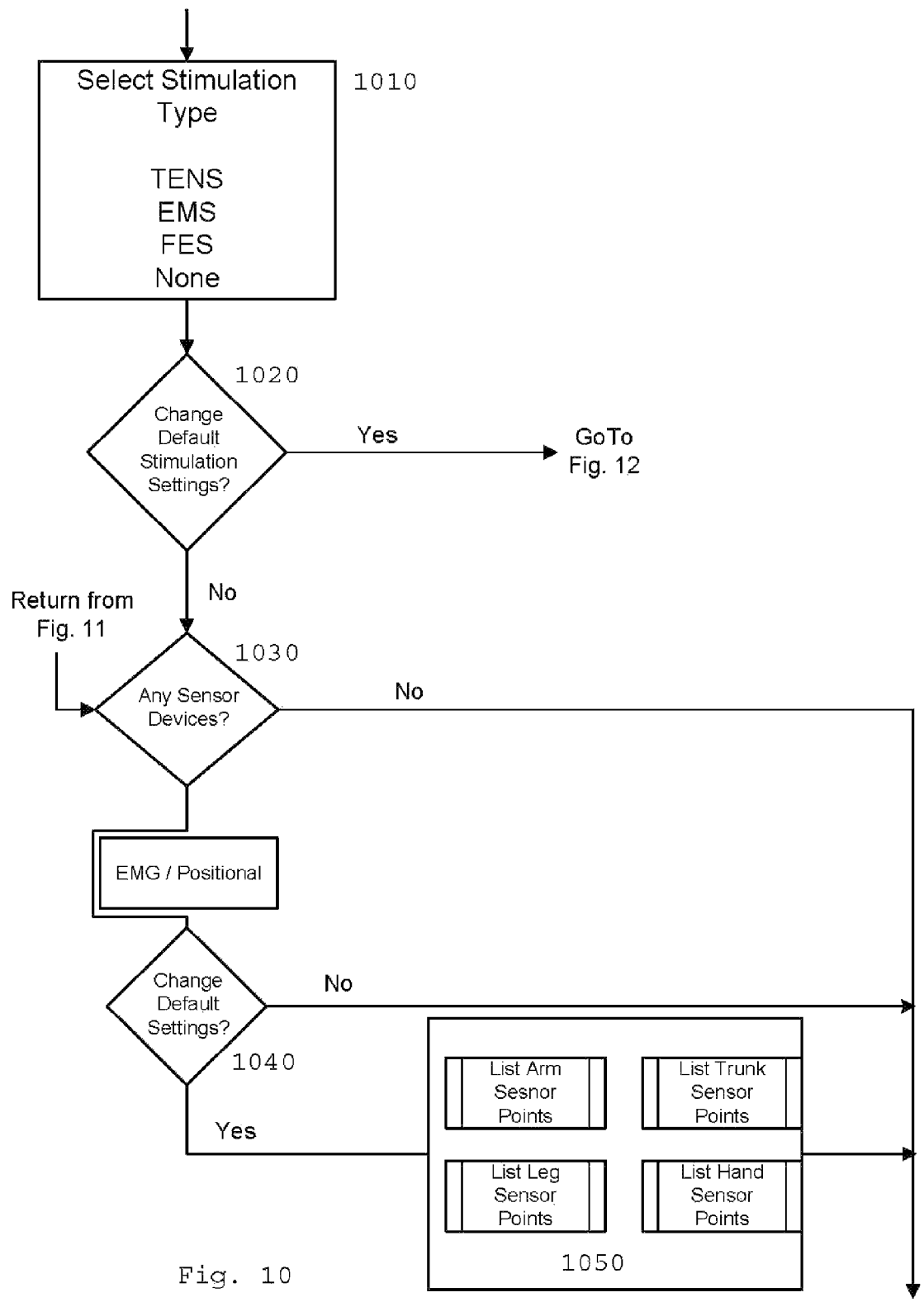
Figure 12:
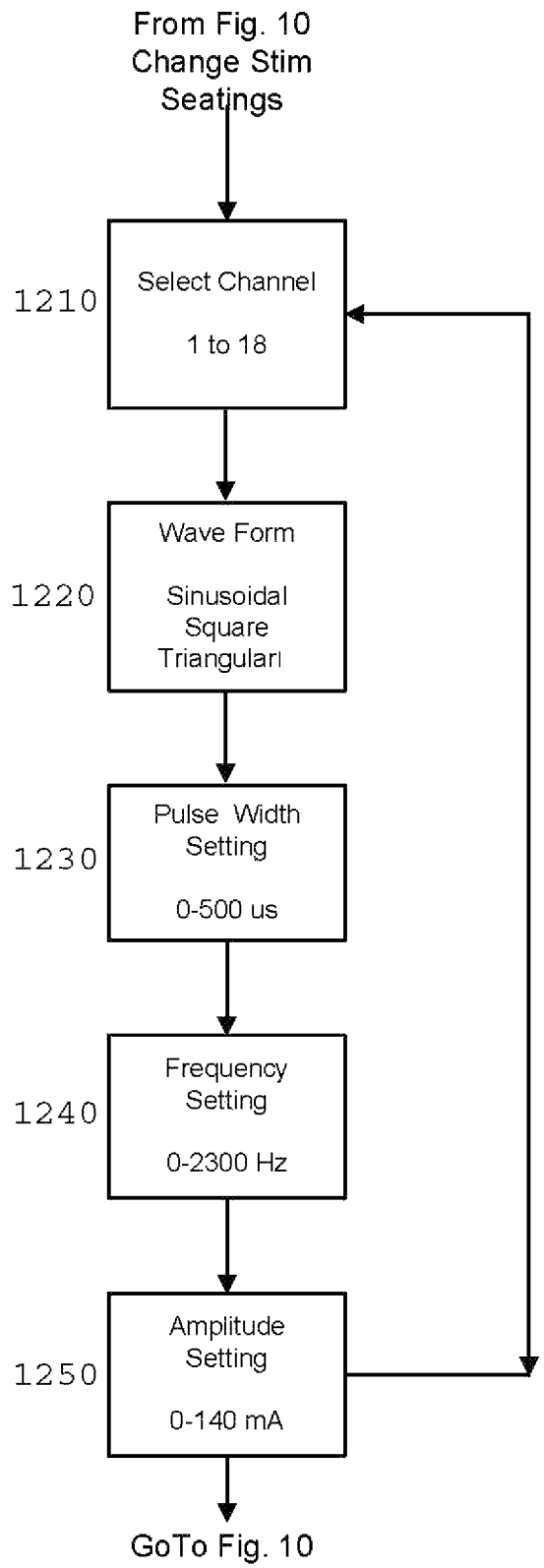

After a stimulation program is selected, a stimulation type may be selected at 1010 in FIG. 10. The stimulation program may apply stimulation types such as TENS, EMS, FES or no stimulation. The user may change the default stimulation settings at 1020. FIG. 12 shows the different stimulation attributes that may be changed by the user. For example, at 1210, the user may select a channel 1 to 18. At 1220, the wave form may be selected from sinusoidal, square or triangular. At 1230, the pulse width setting can be adjusted between 0-500 µs. The frequency setting may be adjusted at 1240 to 0-2300 Hz and the amplitude may be adjusted at 1250 to 0-140 mA.

After the stimulation settings are adjusted or if no changes are needed, the process resumes at 1030, where sensor devices are detected, such as EMG and/or body position sensors (angle accelerometers and gyroscopes). At 1040, those devices default settings may be adjusted. If the settings are adjusted, the sensor points for the selected program (arms, trunk, leg, hands) are listed at 1050.

Figure 11:
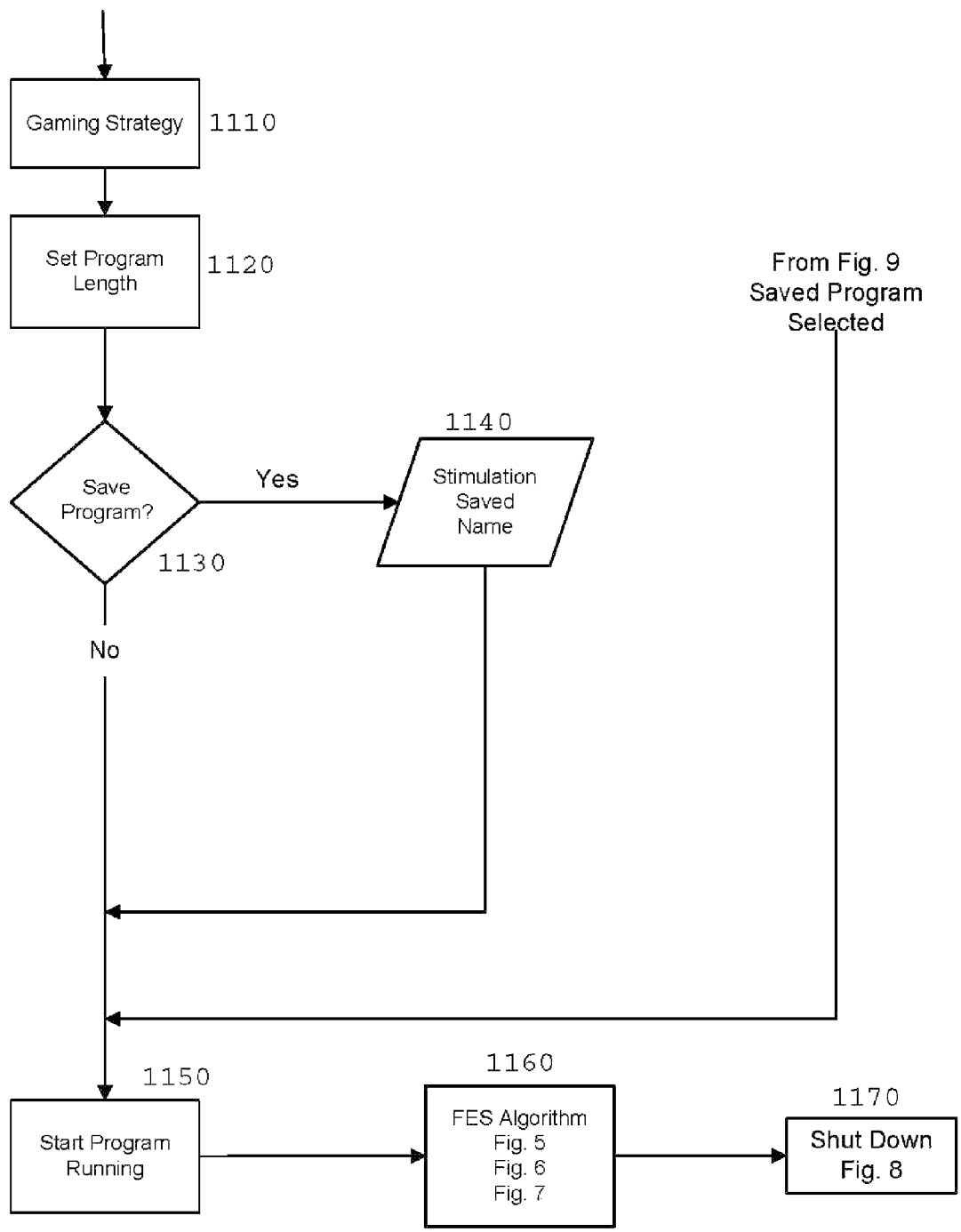

In FIG. 11, a gaming strategy may be selected at 1110. At 1120, the program length is set. A user may save the program at 1130. The program may be saved under a particular name entered by the user at 1140. At 1150 the selected program begins, the FES algorithms used therein at 1160 are now described in more detail.

Figure 5:
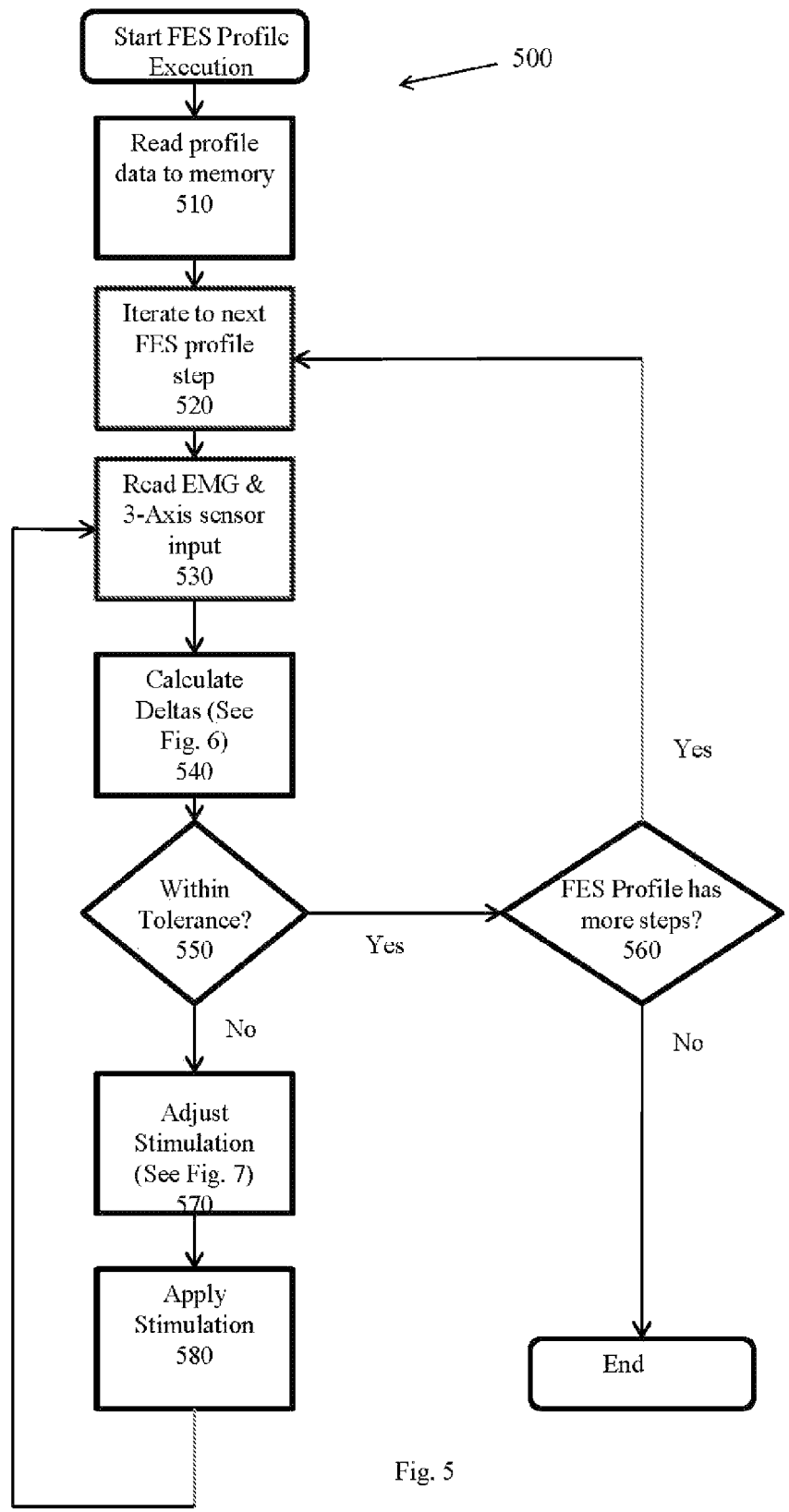
Figure 6:
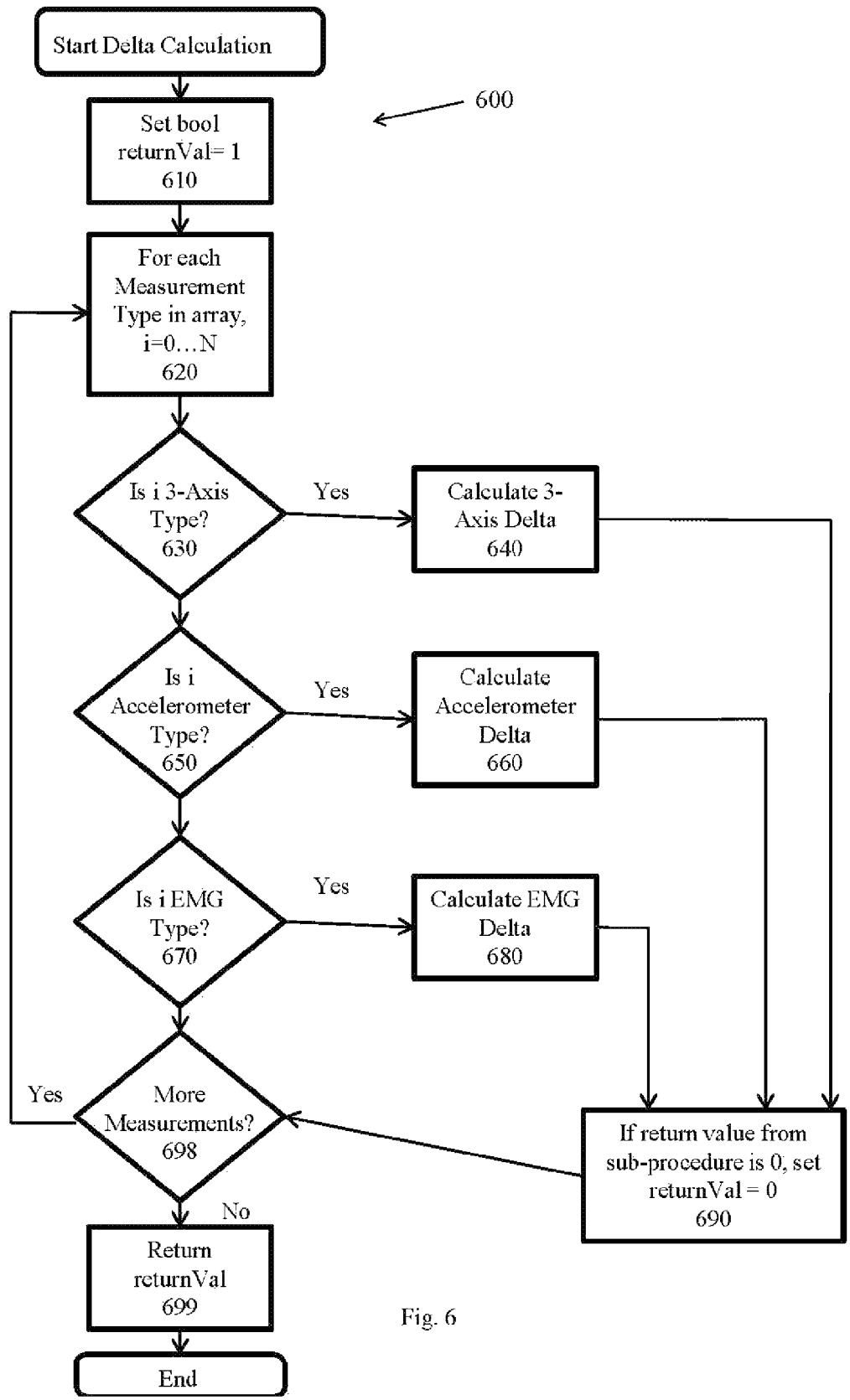
Figure 7:
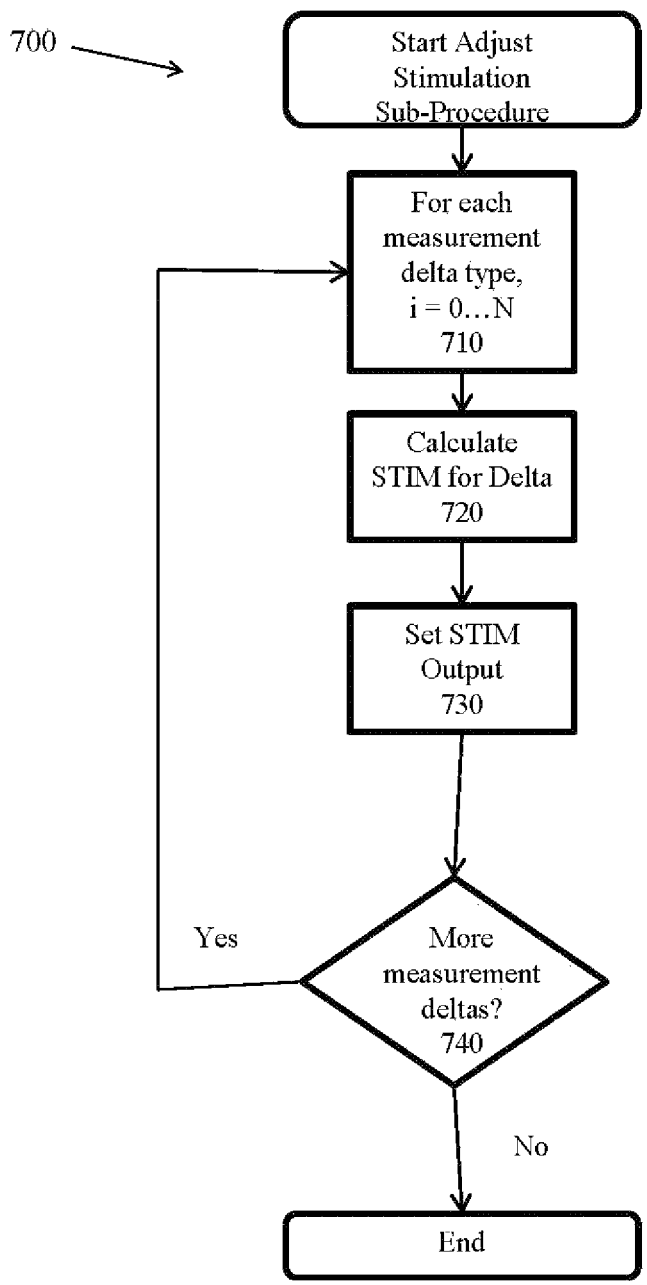

FIG. 5 shows the program being executed according to sub-procedure 500. Sub-procedure 500 in FIG. 5 includes the step of reading profile data to memory 510, and iterating through each FES profile step at 520. Sub-procedure 500 also includes the step of reading EMG and 3-Axis sensor input 530, calculating deltas 540 as shown in FIG. 6, and determining if the deltas are within a tolerance at step 550. If the delta is within a tolerance, the FES profile is analyzed to see if there are more profile steps to iterate through at step 560. If the delta is not within the tolerance, the stimulation is adjusted at 570, as shown in FIG. 7, and the adjusted stimulation is applied at step 580.

FIG. 6 shows sub-procedure 600 for calculating deltas for actual versus ideal body positioning. An example of a definition for sub-procedure 600 follows:

Method Definition:

bool calculateDeltas(struct Measurement Type[ ]
currentConfiguration, struct MeasurementType[ ]
idealConfiguration, struct MeasurementType[ ]* deltas)
Parameters for the method definition include:
struct MeasurementType[ ] currentConfiguration—an
array of measurements observed in real-
time representing the current position and state of the measured body.
struct MeasurementType[ ] idealConfiguration—an
array of measurements observed in real-time
representing the current position and state of the measured body.
struct MeasurementType[ ]* deltas—an out-bound
array of measured discrepecies between
parallel arrays represented by the
currentConfiguration and the idealConfiguration.
Data-Type Definitions:
typedef struct Spatial3AxisInstrumentType {
　　/*Implementation Data*/
};
typedef struct AccelerometerInstrumentType {
　　/*Implementation Data*/
};
typedef struct EMGInstrumentType {
　　/*Implementation Data*/
};
typedef union MeasurementInstrumentType {
　　struct Spatial3AxisInstrumentType* spatial3AxisInstrument = 0;
　　struct AccelerometerInstrumentType accelerometerInstrument = 0;
　　struct EMGInstrumentType EMGInstrument = 0;
};
typedef struct MeasurementInstrumentType {
　　//Can be any of : MEASUREMENT_TYPE_3AXIS,
　　//MEASUREMENT_TYPE_ACCELEROMETER,
　　//MEASUREMENT_TYPE_EMG
　　int measurementInstrument = 0;
　　unionMeasurementInstrumentType* = 0;
};
typedef struct MeasurementDealtaType {
　　//Can be any of : MEASUREMENT_TYPE_3AXIS,
　　//MEASUREMENT_TYPE_ACCELEROMETER,
　　//MEASUREMENT_TYPE_EMG
　　int measurementInstrument = 0;
　　bool isWithinTolerance = 0;
　　float deltaValue = o.o;
};
Return parameters:
1 if the currentConfiguration array contains no measurements that
are out of the profile's defined tolerance. (i.e. Overall body positioning is
"close enough" to correct as defined by the clinician's profile).
0 if any single delta is outside of the profile's defined tolerance.

At step 610 a boolean variable, such as bool calculateDeltas, is set with a return value of 1. At step 620, for each measurement type in an array, for example for each measurement type in struct MeasurementType[ ]currentConfiguration, struct MeasurementType[ ] idealConfiguration, or struct MeasurementType[ ]* deltas, measurement type i=0 . . . N, and the following decisions are made. At step 630, if i is a 3-Axis type, the 3-Axis delta is calculated at step 640. At step 650, if i is an accelerometer type, the accelerometer delta is calculated at step 660. At step 670, if i is an EMG type, the EMG delta is calculated. If the return value of the delta calculation is 0, the return value boolean is set to 0 at step 690. If there are more measurements, for example if i<=N, then at step 698, the sub-procedure is directed back to step 620. If there are no measurements left, the boolean variable return value is returned at 699 and the sub-procedure 600 ends.

Figure 8:
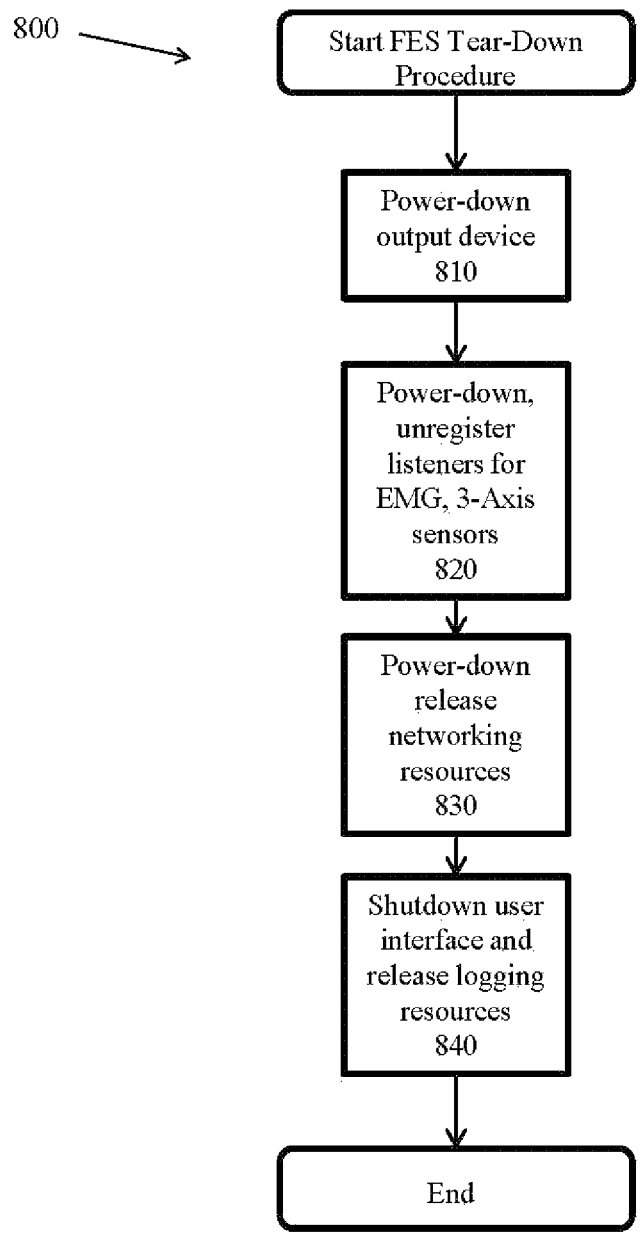
Figure 9:
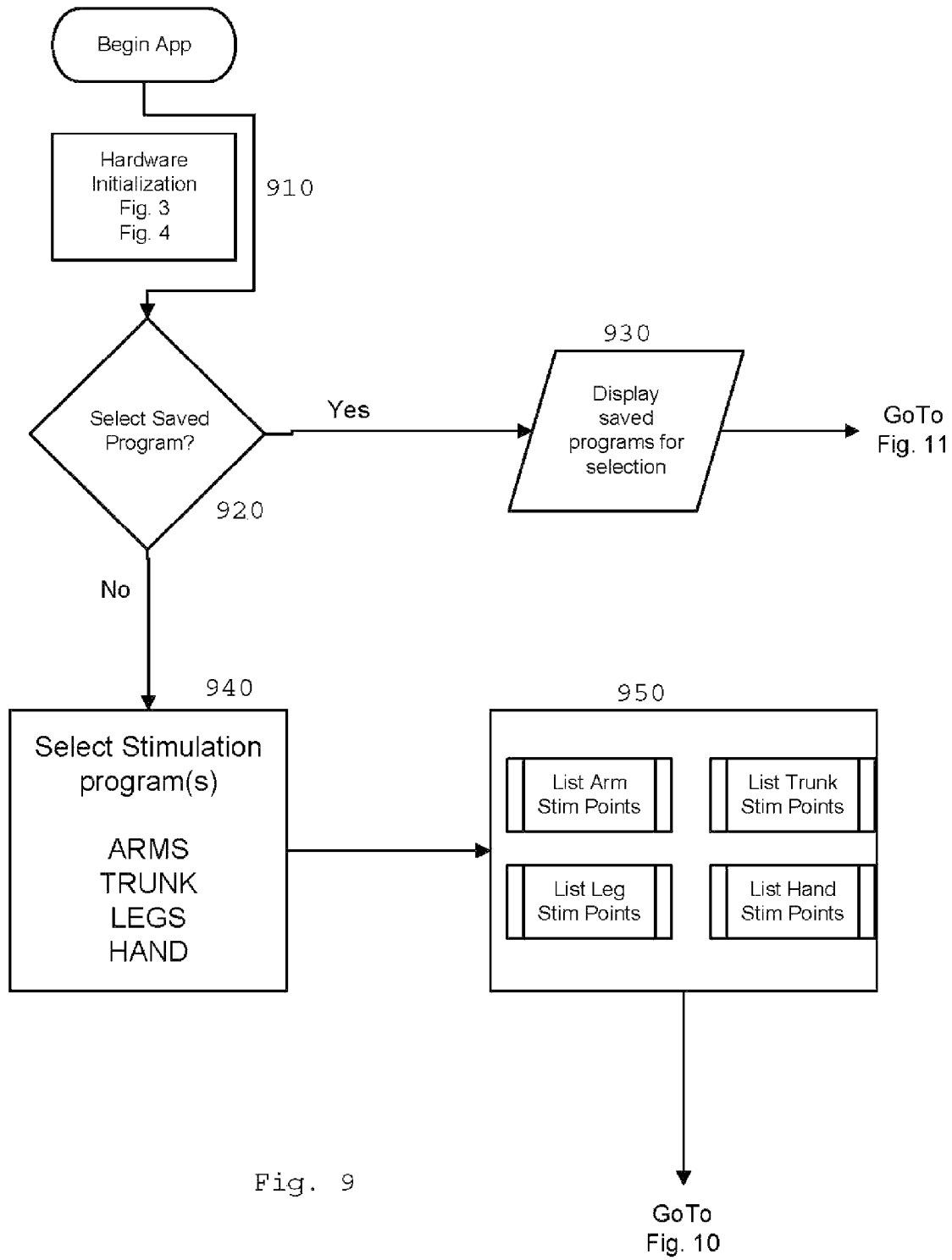
FIGS. 9-12 are flow diagrams showing an example process utilizing the algorithm in FIGS. 3-8 employed with the present invention.

FIG. 7 shows sub-procedure 700 for adjusting stimulation levels if the deltas are not within a tolerance at step 550 of sub-procedure 500. Sub-procedure 700 includes a loop at step 710 for each measurement delta type, i=0 . . . N. At step 720, the STIM is calculated for the delta. At step 730, the STIM output is set based at least upon the calculation at step 720. If there are more measurement deltas at step 740, sub-procedure 700 is set back to step 710. If there are no more measurement deltas, sub-procedure 700 ends. An example of a definition for sub-procedure 700 follows:

Method Definition:

void adjustStimulation(struct StimControlType* step, struct
MeasurementDeltaType[ ] deltas, struct StimControltype[ ]* stimControls)
Parameters:
struct ProfileStepType* step—a struct representing
the current step in the FES profile.
struct MeasurementDeltaType[ ]* deltas—an
array of measured discrepancies between the
ideal configuration and the measured (actual) configuration.
struct StimControlType[ ]* stimControls—an
out-bound array of stim adjustments to be
made to correct for the deltas.
Data-Type Definitions:
typedef struct ProfileStepType{
　　/*Impplementation Detail */
};
typedef struct MeasurementDealtaType {
　　//Can be any of : MEASUREMENT_TYPE_3AXIS,
　　//MEASUREMENT_TYPE_ACCELEROMETER,
　　//MEASUREMENT_TYPE_EMG
　　int measurementInstrument = 0;
　　bool isWithinTolerance = 0;
　　float deltaValue = o.o;
};
typedef struct StimControlType{
　　/*Implementation Detail */
};

FIG. 8 shows FES tear-down sub-procedure 800. Sub-procedure 800 includes power-down of the output device at step 810, power-down and unregistration listeners for EMG, 3-Axis sensors at step 820, power-down release of networking resources at step 830 and shutdown of the user interface and release of logging resources at step 840.

The present universal closed-loop FES system invention can be used to restore function in numerous body parts of persons with neurological impairments (e.g. hand function, core strength, walking, etc) and to catapult FES technology beyond clinical setting to telerehabilitation and gym applications with secure, HIPAA compliant, remote home-based fitness and therapy serving people with paralysis in the convenience of clinics, gyms and their homes. Additionally, this technology application will accelerate commercialization of a full-line of efficient, remotely measured and monitored, economical and user-friendly wearable computer and apparel products. These products will serve the growing global population of people who have 1) chronic health conditions, 2) are overweight and interested in exercise fitness, 3) need motion capture and analysis in business, training and advanced sports performance, and 4) monitoring for military personnel and first responders in dangerous environments, although other applications could be included and so the examples should not be limiting.

The following applications are examples of the use of the present invention, since use of dynamic real-time controls can provide movement, training and regeneration in specified areas, but they are not considered exhaustive:

1. The use of the system for controlling physiological aspects of anatomy under computer control, which enables drive control of muscle tissue with real-time feedback for the purpose of measuring muscle reaction and determining muscle fatigue.
2. The use of a matrix of topical computer controlled (smart) electrodes arranged over a wide area of the anatomy, including analog and digital signaling switch circuitry and movement/placement sensors. The analog and digital signaling switch circuitry enables the driving of FES and the feedback of EMG via the same electrodes. The switch circuitry dynamically enables multiple nodes in the matrix to work in combination to emulate a larger electrode and/or electrodes of varying shape and size and/or and/or advanced skin interfaces.
3. The use of an array of small sensors/electrodes over a large area of anatomy, an autonomous computer controlled algorithm that dynamically stimulates while capturing feedback data to determine an optimal size, shape, and placement of an emulated electrode for the purposes of FES/EMG closed-loop control.
4. The capture of complex muscle movements can be compared to a large template of known movement models.
5. The enablement of movement of disabled parts of an anatomy based upon known good movement models for exercise and therapy.
6. The use of the device to provide real-time integration and control of multi-modalities and machines.
7. The integrated monitoring of vital functions and outcome neurological measures with distance management, while controlling the surface sensory and stimuli system to evaluate, monitor and train a variety of neurological and autonomic functions.
8. The use of the device as a wearable computing system integrated with wearable fabric and/or advanced skin interface encompassed sensory and stimuli measures and deliverables.
9. The use of the device in static cardiovascular exercise, such as for a workout measurement tool and device, the entire body can be covered with a flexible, wearable garment and/or advanced skin interface. Then muscles and large muscle groups are repeatedly activated via FES in an opposing manner to limit physical movement and raise the subject's metabolic rate for the purpose of exercising the heart, build muscle mass, and build bone mass.
10. The use of the present invention as a universal trunk stimulator to help restore motor function to persons with disabilities, and also address FES exercise for people who are overweight and those looking for advanced sports performance.
11. The use of the device in conjunction with constructive electromagnetic interference and/or as a deep tissue stimulation and scanning device.
12. The use of the device as a non-evasive deep tissue stimulation device using a computer controlled array of electrodes surrounding an area of interest, each electrode transmitting an electromagnetic signal into tissue. The overlap of multiple signals creates nodes of both constructive and destructive interference. Computer generation of these signals enables precise placement of interference nodes in the area surrounded by the electrode array.
13. The use of multiple surface electrodes to provide an additive stimulus signal in which a node of constructive interference generates an area of high potential and a node of destructive interference generates an area of low potential. By placing a high potential on one side of a trigger area, and a low potential on the opposite side of a trigger area causes a flow of ions, thus triggering stimulation.
14. The use of a bipolar pair of nodes is placed at a location within the surrounded tissue of an electrode array that can record a reaction (via physical movement and/or EMG feedback). The bipolar pair is then moved a small distance and the process is repeated. Continued movement of the bipolar pair sweeps the entire area of tissue surrounded by the electrode array. Mapping of the corresponding data enables an autonomous means to map out the most optimal sensation points within the area of interest.
15. The use of a computer-controlled array of strategically place EMG electrodes to sample activity and match that activity to movement models enabling accurate prediction of desired movement, other key areas of the anatomy can be electrically stimulated to either cause movement (for the disabled) or enhance movement, and this can enable the movement of disabled and/or paralyzed parts of an anatomy based upon captured and predicted movement of enabled parts of the anatomy.
16. The use of a computer-controlled array of strategically placed (or autonomously configured) EMG electrodes can be used to sample activity and match that activity to movement models enabling accurate prediction of desired movement. Based upon the movement model, other key areas of the anatomy are electrically stimulated via FES to either cause movement (for the disabled) or enhance movement and this will enable the movement of disabled parts of an anatomy based upon captured and predicted movement of enabled parts of the anatomy.
17. The use of the device can be used to maximize stimulation to (or, over stimulate) key muscles and/or muscle groups in an orchestrated and optimized manner to enhance performance at a precise and advantageous moment.
18. The use of the device can be used to dynamically capture complex muscle movements that are then compared to a large template of movement models to predict an activity, then stimulating relative muscles/muscle groups to communicate the best/optimal sequence of movements for a specific activity for learning/training needs.
19. The use of the device can be used for surface stimuli and sensors capabilities to retrain and strengthen body skeletal musculature and associated CNS systems to gain functional control and, where appropriate, to use muscle against muscle to place stress on bone and enhance bone density.
20. The use of the device can be used for dynamic integrated control. These include, but are not limited for trunk, upper and lower extremities, legs, pelvis & shoulder device to facilitate disabled human to computer interface and control by using a select array of EMG electrodes and 3-D sensors measuring muscle and body movements in the upper and lower extremities, shoulder, legs and pelvis.
21. The use of the device to stimulate, repair and control autonomic nervous system function. These may include, but are not limited to, control of bowel and bladder, blood pressure and heart rate, respiration, multiple organ function and sexual function.

22. The use of the system to modulate sensory function via stimulation activity. These include, but are not limited to, light touch, vibration, proprioception and pain.

23. The use of the device to offset aging of the nervous system including limiting or reversing loss of neural cells, neural connections and global CNS function.

24. The use of the device to offset aging or pathological injury to the peripheral nervous system.

25. The use of the device to restore health to end organs such as offsetting aging or reversing injury to end organs. For example, maintaining the multiple organelles of the skin, including vasculature, sensory systems and skin integrity.

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated.

What we claim is:

1. An automated adaptive closed-loop functional electrical stimulation system comprising:
    at least one electrode assembly comprising a plurality of electrodes, including stimulation electrodes, placed on and adapted to deliver an electrical stimulation signal to the central nervous system, peripheral nervous system, or muscles of a user and sensor electrodes adapted to detect a mechanical response to a muscle stimulation signal;
    system means for dynamically mapping the electrode locations in real time to map out the optimal sensation points within an area of interest to enable the stimulation of a plurality of muscles;
    wherein the system is adapted to detect a mechanical response to a muscle stimulation signal of at least one muscle associated with a muscle group stimulated through the nervous system or proximate to the electrode assembly;
    wherein the system includes means for confirming the position of the electrode on the surface of a body and disengaging those electrodes which would affect vital human parts and those electrodes not needed for certain purposes;
    an electrical stimulation device capable of providing an electrical stimulation and operably coupled to said at least one electrode assembly and at least one sensor, the electrical stimulation device including a control system operable to automatically receive feedback from at least one characteristic of the muscle from the detected muscle response and adjust at least one parameter of the muscle stimulation signal in real-time and in response thereto to deliver an adjusted muscle stimulation signal;
    wherein said electrical stimulation device includes means for generating an electrical signal which includes a sequence of pulses having a selected pulse frequency and amplitude, wherein each pulse includes positive and negative excursions relative to a reference voltage;
    means for automatically changing the pulses in the pulse sequence between being initially positive-going and initially negative-going upon the successive occurrence of a predetermined number of pulses in the pulse sequence, thereby producing at least one harmonic frequency in the sequence of pulses in addition to the basic pulse sequence frequency;
    the predetermined number of pulses is more than two; and
    the electrical signal is a non-repeating, nonlinear, randomized wave selected from the group consisting of sinusoidal, square, triangular and combinations thereof; and
    a programmed microprocessor for controlling said electrical stimulation and receiving input from said at least one sensor, including means for comparing said electrical stimulation and said mechanical response based upon the input from said sensor and the means for comparing, wherein said comparing of said electrical stimulation and mechanical response is performed autonomously by said programmed microprocessor, without the need for human adjustment;
    wherein the electrical stimulation and the detected muscle response comprises a plurality of reaction pulses.

2. The system of claim 1, wherein said system includes means for remotely receiving said input and directing said electrical stimulation.

3. The system of claim 1, wherein the system employs more than 10 electrode assemblies incorporated into a form-fitting article of clothing and/or advanced skin interface.

4. The system of claim 1, wherein the sensors include at least one electromyography transducer adapted to be coupled to a body surface adjacent to the muscle being stimulated for generating an output signal indicating the response of said muscle.

5. The system of claim 1, wherein the system further includes an electrical filter means for eliminating unwanted signals and noise from said input signals.

6. The system of claim 1, wherein the system further includes a means for amplifying said input signals and controlling the amplification range of said input signals.

7. The system of claim 1, wherein the system further includes means for displaying the intensity of said input signals.

8. The system of claim 1, wherein the sensors include at least one accelerometer, at least one magnetometer, and at least one gyroscope for measuring movement of a body part associated with the muscle being stimulated.

9. The system of claim 1, wherein said electrical stimulation provides a supplement to exercise.

10. The system of claim 1, wherein the system further includes an electromagnetic stimulation device.

11. The system of claim 1, wherein said electrode assembly is attached to a trunk, upper or lower extremities, pelvis, shoulder, or any combination thereof.

12. The system of claim 1, wherein the sensors include at least one 3-axis sensor for measuring movement of a body part.

13. The system of claim 1, wherein the sensors include a means for analyzing an EMG signal for sensing muscle fatigue.

14. The system of claim 1, wherein said electrical stimulation provides deep tissue stimulation using at least one of constructive interference and destructive interference, from two or more electrodes.

15. An automated adaptive functional electrical stimulation system comprising:
    at least one electrode assembly adapted to deliver a spinal cord stimulation signal to the spinal cord of a user;
    a sensor system, comprising at least one accelerometer, at least one magnetometer, and at least one gyroscope, adapted to detect a mechanical response to 1] the muscle stimulation signal of at least one muscle associated with a muscle group which would receive input from the electrode assembly and 2] to a volitional activation of a muscle by the user;

an electrical stimulation device operably coupled to the at least one electrode assembly and one sensor system, the electrical stimulation device including a control system operable to automatically diagnose at least one characteristic of the muscle from the detected mechanical response and/or adjust at least one parameter of the muscle stimulation signal in response thereto to deliver an adjusted muscle stimulation signal; and a programmed microprocessor for controlling said electrical stimulation and receiving input from said sensor system, means for comparing, in real time, the electrical stimulation and the mechanical response, wherein the detected muscle response comprises a plurality of reaction pulses, and wherein the control system is operable to provide real time sensor and electrode mapping and real time analysis and adjust the electrical stimulation based upon the comparison of the electrical stimulation and the input from the sensor system;

wherein said spinal cord stimulation provides stimulation using at least one of constructive interference and destructive interference, from two or more electrodes.

16. An automated adaptive closed-loop functional electrical stimulation system comprising:

at least one electrode assembly comprising a plurality of electrodes, including stimulation electrodes, placed on and adapted to deliver an electrical stimulation signal to the central nervous system, peripheral nervous system, or muscles of a user and sensor electrodes adapted to detect a mechanical response to a muscle stimulation signal;

system means for dynamically mapping the electrode locations in real time to map out the optimal sensation points within an area of interest to enable the stimulation of a plurality of muscles;

wherein the system is adapted to detect a mechanical response to a muscle stimulation signal of at least one muscle associated with a muscle group stimulated through the nervous system or proximate to the electrode assembly;

an electrical stimulation device capable of providing an electrical stimulation and operably coupled to said at least one electrode assembly and at least one sensor, the electrical stimulation device including a control system operable to automatically receive feedback from at least one characteristic of the muscle from the detected muscle response and adjust at least one parameter of the muscle stimulation signal in real-time and in response thereto to deliver an adjusted muscle stimulation signal;

wherein said electrical stimulation device includes means for generating an electrical signal which includes a sequence of pulses having a selected pulse frequency and amplitude, wherein each pulse includes positive and negative excursions relative to a reference voltage;

wherein said electrical stimulation provides deep tissue stimulation using at least one of constructive interference and destructive interference, from two or more electrodes;

means for automatically changing the pulses in the pulse sequence between being initially positive-going and initially negative-going upon the successive occurrence of a predetermined number of pulses in the pulse sequence, thereby producing at least one harmonic frequency in the sequence of pulses in addition to the basic pulse sequence frequency;

the predetermined number of pulses is more than two; and the electrical signal is a non-repeating, nonlinear, randomized wave selected from the group consisting of sinusoidal, square, triangular and combinations thereof; and a programmed microprocessor for controlling said electrical stimulation and receiving input from said at least one sensor, including means for comparing said electrical stimulation and said mechanical response based upon the input from said sensor and the means for comparing, wherein said comparing of said electrical stimulation and mechanical response is performed autonomously by said programmed microprocessor, without the need for human adjustment;

wherein the electrical stimulation and the detected muscle response comprises a plurality of reaction pulses.

17. The system of claim 16, wherein the system further includes an electromagnetic stimulation device.

18. The system of claim 16, wherein the sensors include at least one 3-axis sensor for measuring movement of a body part.

19. The system of claim 16, wherein the sensors include a means for analyzing an EMG signal for sensing muscle fatigue.

20. The system of claim 16, wherein the system includes means for confirming the position of the electrode on the surface of a body and disengaging those electrodes which would affect vital human parts and those electrodes not needed for certain purposes.

* * * * *